US006743782B1

(12) United States Patent
Von Borstel et al.

(10) Patent No.: US 6,743,782 B1
(45) Date of Patent: Jun. 1, 2004

(54) ACYL DEOXYRIBONUCLEOSIDE DERIVATIVES AND USES THEREOF

(75) Inventors: Reid W. Von Borstel, Kensington, MD (US); Michael K. Bamat, Chevy Chase, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 09/494,242

(22) Filed: Jan. 31, 2000

Related U.S. Application Data

(63) Continuation of application No. 08/153,163, filed on Nov. 17, 1993, now Pat. No. 6,020,320, which is a division of application No. 07/958,598, filed on Oct. 7, 1992, now abandoned, which is a continuation of application No. 07/533,933, filed on Jun. 5, 1990, now abandoned, which is a continuation of application No. 07/115,923, filed on Oct. 28, 1987, now abandoned.

(51) Int. Cl.$^7$ .............................................. A61K 31/70
(52) U.S. Cl. ............................ 514/46; 514/45; 514/49; 514/50
(58) Field of Search ............................. 514/46, 45, 49, 514/50

(56) References Cited

U.S. PATENT DOCUMENTS

| | | |
|---|---|---|
| 3,585,188 A | 6/1971 | Marumoto et al. |
| 3,847,898 A | 11/1974 | Kelly |
| 3,894,000 A | 7/1975 | Wechter et al. |
| 3,975,367 A | 8/1976 | Gish et al. |
| 3,991,045 A | 11/1976 | Ishida et al. |
| 4,048,432 A | 9/1977 | Baker |
| 4,208,406 A | 6/1980 | Lapinet et al. |
| 4,560,678 A | 12/1985 | Ranson |
| 4,657,896 A | 4/1987 | Yano et al. |
| 4,675,189 A | 6/1987 | Kent et al. |
| 4,757,139 A | 7/1988 | Kawaguchi et al. |
| 4,758,553 A | 7/1988 | Ogoshi |
| 4,868,162 A | 9/1989 | Kawaguchi et al. |
| 5,246,708 A | 9/1993 | von Borstel et al. |
| 6,020,320 A | * 2/2000 | von Borstel et al. .......... 514/46 |

FOREIGN PATENT DOCUMENTS

| | | |
|---|---|---|
| DE | 3319282 | 11/1983 |
| EP | 0056265 | 7/1982 |
| EP | 0222192 | 5/1987 |

OTHER PUBLICATIONS

Ensminger et al, the Chemical Abstracts, 92: 87921x (1980).

Narang et al, the Chemical Abstracts, 83: 147700a (1975).

Adamiak et al, the Chemical Abstracts, 106: 156803g (1987).

Pfleiderer, the Chemical Abstracts, 107: 218016j (1987).

Blood, 74(6) 1923–1928 (1989).

Cancer Treatment Reports, 69(7–8), 851–857 (1985).

Chemical Abstracts, vol. 74, No. 112368k, Rajabalee, Angew. Chem. Int. Ed Engl. 10(1): 75 (1971).

Biochemistry, vol. 13, No. 3, Jan. 29th 1974, pp. 553–559; M.J. Robins et al: "3'–0–aminoacyl–2'–deoxyadenosines and 2'–0–aminoacyl–3'–deoxyadenosines related to charged transfer ribonucleic acid termini".

(List continued on next page.)

*Primary Examiner*—James O. Wilson
(74) *Attorney, Agent, or Firm*—Nixon & Vanderhye

(57) ABSTRACT

The invention relates to compositions comprising acyl derivates of 2'-deoxyribonucleosides. The invention also relates to methods of treating or preventing radiation, mutagen and sunligth-induced cellular damage, methods for improving wound healing and tissue repair, and methods for ameliorating the effects of aging comprising administering the composition of the present invention to an animal.

8 Claims, 3 Drawing Sheets

OTHER PUBLICATIONS

Biochemistry, vol. 14, No. 14, Jul. 15th 1974, pp. 3144–3151; S.P. Dutta et al: "Synthesis and properties of the naturally occuring N–[9–beta–D–ribofuranosylpurin–6–yl)–N–methylcarbamoyl]–L–threonine (mt6A) and other related synthetic analogs".

Biochemistry, vol. 20, No. 1, Jan. 6th 1981, pp. 8–15, American Chemical Society; A Bhuta et al: "Stereochemical control of ribosomal peptidyltransferase reaction. Role of amino acid side–chain orientation of acceptor substrate."

Biochemistry, vol. 20, No. 12, Jun. 9th 1981, pp. 3480–3485, American Chemical Society; K. Quiggle et al: "Donor Site of Ribosomal Peptidyltransferase: Investigation of Substrate specificity using 2'(3')–0–(N–acylaminoacyl)dinucleoside phosphates as models of the 3'terminus of N–acylaminoacyl transfer ribonucleic acid."

Journal of American Chemical Society, vol. 104, No. 2, 1982, pp. 544–547, American Chemical Society; G. Buchi et al: "Photochemical epoxidation of aflatoxin B1 and sterigmatocystin: Synthesis of Guanine–Containing adducts."

Pure and Applied Chemistry, vol. 52, No. 12, 1980, pp. 2705–2715, IUPAC GB; T. Matsuura et al: "Organic Chemical Approach to Photo–Cross–Links of Nucleic Acids to Proteins".

Journal of Carbohydrate Nucleosides Nucleotides, vol. 4, No. 6, 1977, pp. 387–408, Marcel Dekker, Inc., E.K. Ryu et al; "Aminoacyl Derivatives of Nucleosides, Nucleotides, and Polynucleotides. XXVII. General Synthesis of 2'(3')–O–Aminoacyl Dinucleoside Phosphates Derived from the AA–tRNA terminus."

Golba, et al, *Int. J. Rad. Biol.* 13:261–268 (1967).
Goh et al, *Proc. Soc. Exp. Biol. Med.* 145:938–943 (1974).
Horikawa, et al, *Exp. Cell. Res.* 34:198–200 (1964).
Pantic, et al, *Nature* 193:993–994 ((1962).
Paoletti, et al, *Rev. Francais. Etudes Clin. et Bio.* 9:950–955 (1964).
Petrovic, et al. *Int. J. Radiat. Biol.* 18:243–258 (1970).
Petrovic, et al, *Studia Biophysica* 43:13–18 (1974).
Petrovic, et al, *Int. J. Radiat. Res.* 11:609–611 (1967).
Savkovic et al, *Nature* 203:1297–1298 (1964).
Savkovic et al, *Nature* 211:1179–1180 (1966).
Savkovic et al, *Int. J. Rad. Biol.* 9:361–368 (1965).
Smets, et al, *Int. J. Rad. Biol.* 13:269–273 (1967).
Soska et al, *Folia Biologica* 5:190–198 (1959).
Sugahara et al, *Brookhaven Symposia in Biology*, 284–302 (1967).
Wagner, *Int. J. Rad. Biol.* 12:101–112 (1967).
Wilczok et al, *Int. J. rad. Biol.* 9:201–211 (1965).
Goyanes–Villaescusa et al, *Lancet* 2:575–576 (1973).
Dumont, *Ann. Surg.* 150:799–807 (1959).
Nicolau et al, *Der Hautarzt*, 17:512–515 (1966).
Marshak et al, *Proc. Soc. Exp. Biol. Med.* 58:62–63 (1945).
Newman et al, *Am. J. Physiol.* 164:251–253 (1951).
Casida et al, *Biochemical Pharmacology* 15:627–644 (1966).
Fridovich, *Annu. Rev. Biochem.* 44:147–159 (1975).
Leukemia, 2(10) 109–110 (1988).
Nair et al, the Chemical Abstracts, 101: 192382z (1984).
Ishido et al, the Chemical Abstracts, 92: 59149h (1980).
Ensminger et al, Biochem. Pharm., 28, 1541–1545 (1979) Thymidine 5'–O–pivaloate.
Rosowsky, Cancer Treatment Reports, 65 (1–2), 93–98 (1981).
Morrison and Boyd, Fourth Edition, "Organic Chemistry" Allyn and Bacon, Inc., Boston, 1983.
Kanazir et al, *Bull. Inst. Nuc. Sci. "Boris Kidrich"* 9:145–153 (1959).
Beltz et al, *Bioch. Biophys. Acta* 297:258–267 (1973).
Hunting, D.J., et al, *Carcinogensis* 6:1525–1528 (1985).

* cited by examiner

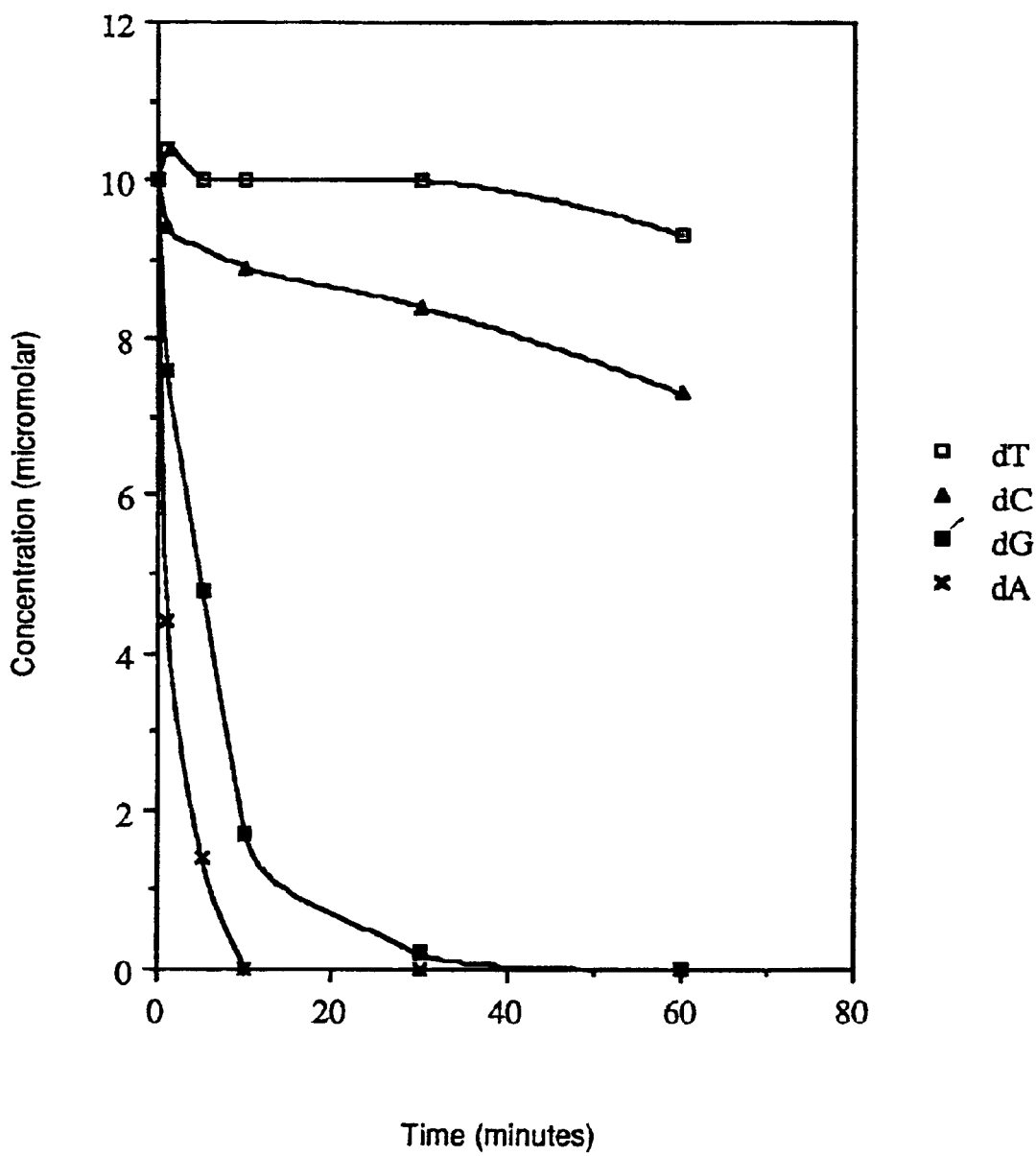
Fig.1: Degradation of Deoxynucleosides in Plasma

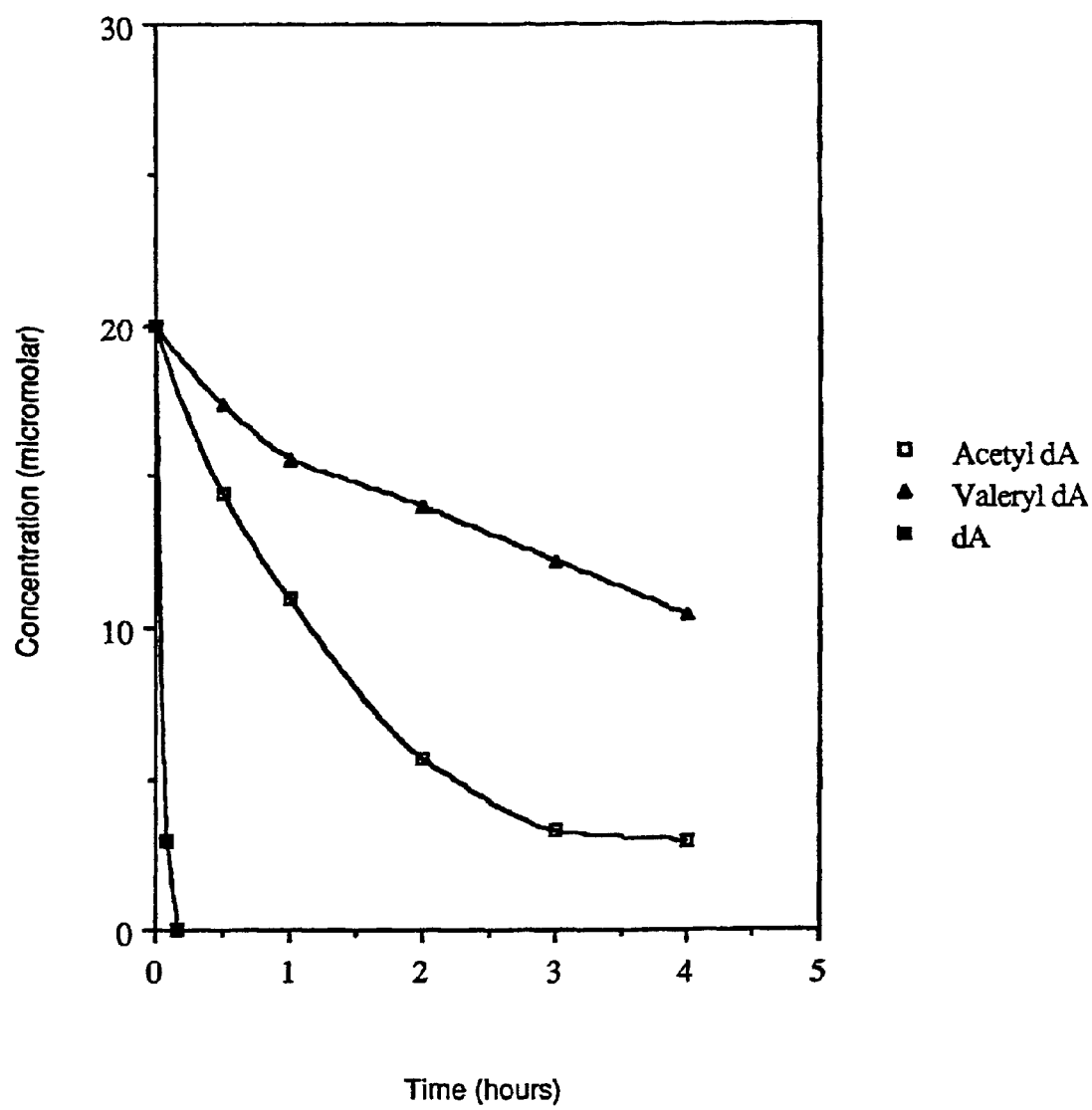
Fig. 2: Disappearance of deoxyadenosine derivatives in plasma

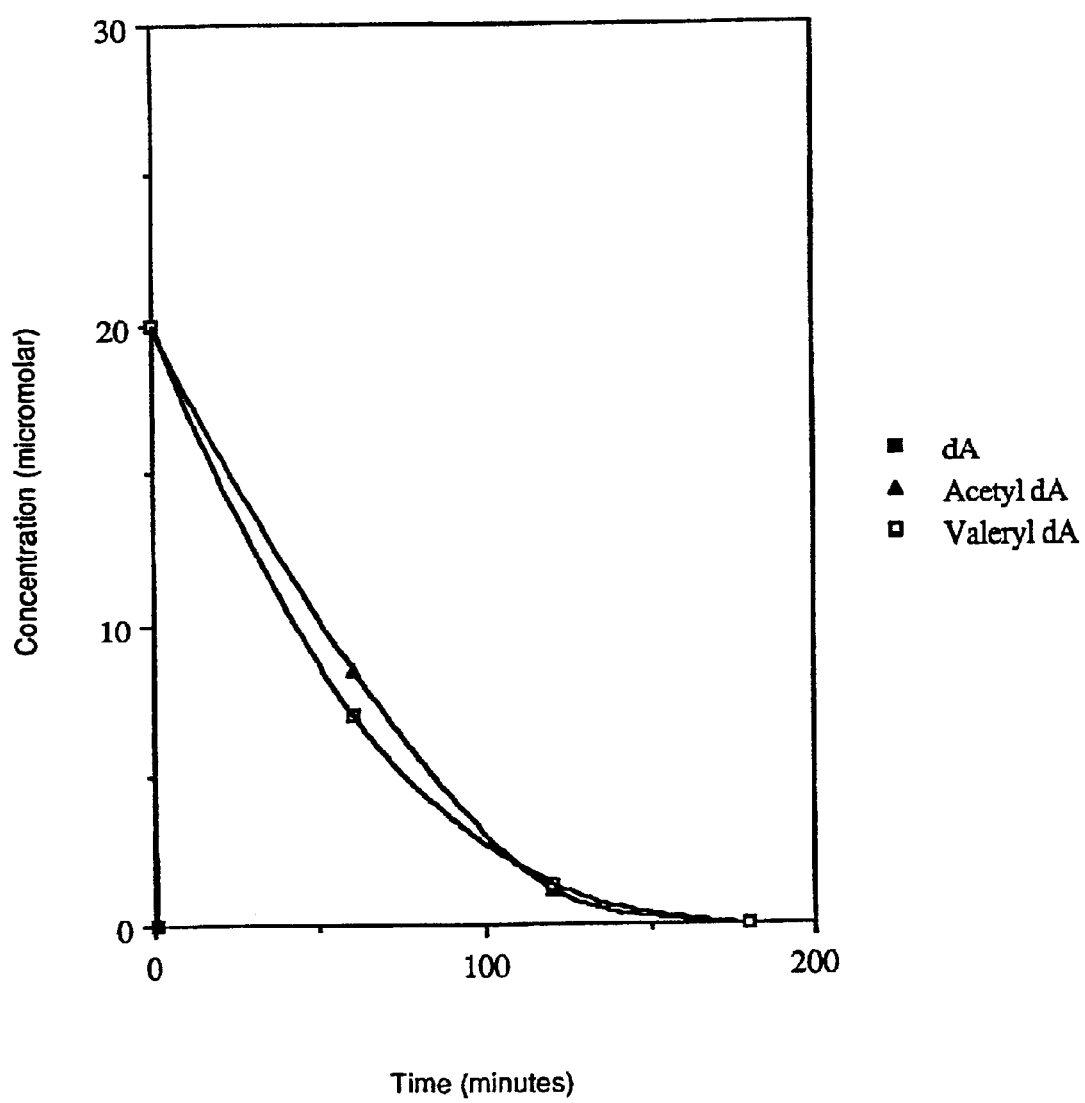
Fig. 3: Disappearance of deoxyadenosine derivatives in liver

ACYL DEOXYRIBONUCLEOSIDE DERIVATIVES AND USES THEREOF

This application is a Continuation of application Ser. No. 08/153,163, filed Nov. 17, 1993, now U.S. Pat. No. 6,020,320, which is a Divisional of Ser. No. 07/958,598, filed Oct. 7, 1992, now abandoned, which is a Continuation of Ser. No. 07/533,933, filed Jun. 5, 1990, now abandoned, which is a Continuation of Ser. No. 07/115,923, filed Oct. 28, 1987, now abandoned, the contents of which are hereby incorporated by reference in this application.

FIELD OF THE INVENTION

This invention relates generally to acyl derivatives of deoxyribonucleosides and to the use of those derivatives to enhance the delivery of exogenous deoxyribonucleosides to animal tissue. More specifically, this invention relates to the acyl derivatives of 2'-deoxyadenosine, 2'-deoxyguanosine, 2'-deoxycytidine and 2'-deoxythymidine and the use of those novel derivatives to increase the bioavailability of the deoxyribonucleosides to animal tissue and thereby to support cellular metabolic functions. Even more specifically, this invention relates to the use of the novel acyl derivatives to treat or prevent a variety of physiological and pathological conditions in cell tissue, including damage by radiation, sunlight, mutagens, wounds, and other conditions.

BACKGROUND OF THE INVENTION

There are many physiological and pathological conditions of animal tissue where the supply of exogenous deoxyribonucleosides may have useful therapeutic applications. In the treatment of wounds, repair of liver tissue, promotion of repair and survival after radiation, and numerous other conditions, the supply of DNA and/or deoxyribonucleosides at a high and sustained level may substantially improve the natural DNA and tissue repair processes of the affected cells.

In promoting wound healing, liver regeneration, recovery from radiation damage, and in other pathological and physiological conditions, it is likely that exogenously supplied DNA serves merely as a storage depot for deoxyribonucleosides. That depot gradually releases deoxyribonucleotides and deoxyribonucleosides during enzymatic degradation. Thus the administration of deoxyribonucleosides or derivatives disclosed herein may have value as a method for delivering those deoxyribonucleosides to tissues, which method is preferable to the administration of foreign DNA insofar as wound healing, tissue regeneration, recovery from irradiation, and the like, is concerned.

A number of investigators have attempted to use DNA and/or deoxyribonucleosides to treat a variety of conditions in experimental animals and to enhance or augment cellular repair processes, including DNA repair. It has been demonstrated that administration of exogenous DNA to experimental animals after exposure to ionizing radiation can result in dramatically increased survival and functional recovery. Studies on cell cultures in vitro demonstrate that the actual restorative agents are probably deoxyribonucleosides, the enzymatic degradation products of DNA. These compounds enhance the actual repair of damaged DNA in vitro. However, depolymerized DNA or deoxyribonucleosides administered to animals were ineffective in promoting survival or recovery after irradiation. Kanazir et al., *Bull. Inst. Nuc. Sci "Boris, Kidrinch"* 9:145–153 (1959). There is reason to believe that this apparent contradiction is due to the rapid catabolism of deoxyribonucleosides in vivo by the liver and other organs. Thus, after administration of deoxyribonucleosides, tissues were only exposed to effective concentrations for a matter of minutes. Beltz, et al., *Bioch. Biophys. Acta* 297:258–267 (1973). In cell cultures, optimum survival after irradiation was found when deoxyribonucleosides were present in the incubation medium for at least 3 hours. When DNA is administered by intraperitoneal injection, it is gradually depolymerized to give a sustained release of free deoxyribonucleosides into the circulation. DNA is not, however, a suitable pharmaceutical agent to administer to humans, either orally or parenterally.

Hunting, D. J., et al., *Carcinogenesis* 6:1525–1528 (1985), disclose that deoxyribonucleotide synthesis is rate limiting for excision repair of UV-induced DNA damage. The authors found that there was an increase in repair ligation in cells made permeable to added deoxyribonucleotide triphosphates.

Golba, S., et al., *Int. J. Rad. Biol.* 13:261–268 (1967), disclose that after whole-body irradiation, administration of heterologous DNA improved survival and accelerated the rate of recovery of body weight and of red blood cells, granulocytes and lymphocyte counts in the peripheral blood. No secondary disease or change in the blood count was observed in the next 12 months. Goh, K., *Proc. Soc. Exp. Biol. Med.* 145:938–943 (1974), discloses addition of exogenous deoxyribonucleotides resulted in prevention or healing of "pulverized" chromosomes found in cultures of leukocytes taken from a human subjected to accidental exposure to fast neutron and gamma irradiation. Horikawa, M., et al., *Exp. Cell Res.* 34:198–200 (1964), disclose the effect of the addition of various cell extracts and compounds to an incubation medium containing mouse L cells in culture which were irradiated in culture with X-irradiation (2000 R). Homogenates of L cells, L cell nuclei, or purified DNA from either L cells or salmon sperm all strongly enhanced the survival of the irradiated cells. RNA from either yeast or L cells was found to be ineffective. The authors suggest that the DNA hydrolysates (e.g., deoxynucleotides) are the actual reactivating agents, since heterologous DNA is as effective as homologous DNA.

Pantic, V., et al., *Nature* 193:993–994 (1962), disclose administration of DNA to X-irradiated rats given lethal doses of radiation. The authors found that while DNA treatment did not totally prevent cellular damage in the intestine and liver after irradiation, tissue structure and function were much closer to normal in DNA-treated animals examined 4 or 9 days after irradiation than in untreated irradiated controls.

Paoletti, C., et al., *Rev. Francais. Etudes Clin. et Bio.* 9:950–955 (1964), disclose a study on the effect of administration of DNA and 2-aminoethyl-isothiouronium (AET) to rats. Mice were given a mixture of AET and thiogel orally, then irradiated (700 rad) and subsequently given i.p. injections of 1 mg calf thymus DNA. The mice receiving the DNA injections recovered their weight and initial leukocyte counts more rapidly than mice similarly treated but not receiving the DNA injections.

Petrovic, D., et al., *Int. J. Radiat. Biol.* 18:243–258 (1970), disclose evidence concerning the molecular basis of the restorative effect of DNA in cultured mammalian cells. The authors found that the survival of irradiated cells in culture was enhanced by the addition of either DNA or equimolar amounts of deoxyribonucleosides. DNA was effective only if serum containing active deoxyribonuclease was present in the incubation medium. Thus, the authors concluded that the deoxyribonucleosides were probably the actual reactivating factors responsible for repair of radiation-induced damage. In another study, Petrovic disclosed that maximal restoration is attained when deoxyribnucleosides are in the incubation medium for at least 3 hours after irradiation. The best restoration was achieved with either a mixture of all four major deoxyribonucleosides, or a combination of deoxyguanosine with either deoxyadenosine or deoxycytidine. Petrovic, D., et al., *Studia Biophysica* 43:13–18 (1974). Petrovic et al. also report that in irradiated HeLa cells, treatment with a mixture of the four major deoxyribonucleosides increased survival. Petrovic et al., *Int. J. Radiat. Res.* 11:609–611 (1967).

Savkovic, N., *Nature* 203:1297–1298 (1964), discloses that 8 or 17 day old rats subjected to X-radiation (600 rem), and immediately treated with homologous testes DNA, had a much higher fertility rate than did untreated irradiated controls. Histological studies demonstrated that DNA treatment after irradiation markedly protected the structural integrity of the testes and the function of the spermatogenic processes. Savkovic also reported that heterologous DNA extracted from various organs of adult rats was effective in enhancing the survival of mice subjected to irradiation. The DNA reduced the effects of radiation by a factor of 9 to 13. Savkovic, N., et al., *Nature* 211:1179–1180 (1966). Savkovic, N., et al., *Int. J. Rad. Biol.* 9:361–368 (1965) also disclose that treatment of irradiated rats with homologous DNA, isolated from liver, thymus and spleen, increased survival and fertility of the survivors. The death rate of the progeny of the irradiated rats was strongly reduced in the case of animals that received DNA after irradiation.

In another study, exposure of cultured calf liver cells to X-radiation was found to cause chromosomal damage. When cells were incubated with either DNA or equimolar concentration of deoxyribonucleotides after irradiation, there was a marked reduction in the incidence of chromosome damage. A mixture of dAMP and dGMP was as effective as a mixture of all four major deoxyribonucleotides. Ribonucleotides were ineffective in preventing radiation-induced chromosome damage. Smets, L. A., et al., *Int. J. Rad. Biol.* 13:269–273 (1967).

In a related study, administration of dCMP or dTMP to irradiated mice was found to improve the restoration of hematopoietic function. Soska, J., et al., *Folia Biologica* 5:190–198 (1959).

In another study of mice irradiated with gamma radiation, administration of either a yeast RNA hydrolysate, an equimolar mixture of 3'-nucleotides or a mixture of nucleosides resulted in a significant prolongation of life span. However, long-term survival was not enhanced. The nucleic acid derivatives were administered 30 minutes, 2 days, and 4 days after irradiation. The author observed that the nucleosides, nucleotides, and RNA hydrolysate did not increase the number of surviving stem cell colonies in spleen or bone marrow, but rather appeared to improve the functional capacity of irradiated cells during the critical period after irradiation. These compounds also appeared to accelerate the process of maturation and differentiation of the progeny of surviving stem cells. Sugahara, T., et al., *Brookhaven Symposia in Biology*, 284–302 (1967).

In a study of guinea pigs subjected to X-radiation, animals given RNA or ATP immediately before and after irradiation had much higher 21-day survival rates than did untreated irradiated controls. Most of the animals that survived the 21-day observation period recovered fully, with no secondary radiation-induced disease. Wagner, R., *Int. J. Rad. Biol.* 12:101–112 (1967).

In another study, administration of DNA from different sources, including calf thymus, rat liver and spleen, herring and salmon sperm, and Ehrlich ascites carcinoma cells was studied in rats given lethal doses of gamma irradiation. All forms of DNA significantly increased the survival of the irradiated rats. The quantitative differences in the effects of the DNA from different sources were directly related to the molecular weight. The authors found a reduction in therapeutic efficiency which is proportional to the reduction in molecular size upon DNA shearing. Wilczok, T., et al., *Int. J. Rad. Biol.* 9:201–211 (1965).

The incidence of chromosomal abnormalities in lymphocytes from radiologists chronically exposed to X-rays, was determined before, during, and after treatment with DNA and ATP. The basal incidence of chromosomal damage was substantially higher than in unexposed control subjects. Daily injection of DNA and ATP resulted in 2 to 3 fold decreases in the frequency of chromosomal abnormalities. Following discontinuation of treatment, the incidence of chromosomal damage returned toward pretreatment levels. (Goyanes-Villaescusa, *Lancet* II:575 (1973).

There have also been reports on the use of DNA preparations to treat wounds. For example, Dumont, *Ann. Surg.* 150:799 (1959), disclose that exogenous DNA, applied to experimental wounds in rabbit ears, accelerated the growth of granulation tissue in the wounds. A mixture of DNA plus deoxyribonuclease (the enzyme primarily responsible for degradation of DNA) was more effective in accelerating fibroplasia than either DNA or deoxyribonuclease alone. The total amount of granulation tissue formed after treatment with DNA was not greater than in untreated controls; the onset and rate of its growth were however significantly accelerated. The authors suggest that low polymer DNA fragments are the actual active agents.

Nicolau et al., *Der Hautartzt* 17:512 (1966), disclose a study on experimental skin wounds on the backs of rats which were treated daily with a It solution of DNA in physiological saline. The wounds treated with local application of DNA were cicatrized within four to eight days; those treated only with physiological saline were cicatrized only after 10 to 15 days.

Marshak et al., *Proc. Soc. Exp. Biol. Med.* 58:62 (1945), disclose that application of DNA to experimental skin wounds in rats resulted in a significant acceleration of the growth of granulation tissue within the wounds, as compared to untreated controls. Although the granulation tissue appeared sooner in treated wounds, the final amount of granulation tissue was not abnormal.

Newman et al., *Am. J. Physiol.* 164:251 (1951), disclose a study of rats subjected to partial hepatectomy. The course of liver regeneration was followed for 11 days. The livers of rats treated with DNA regenerated significantly faster than livers in untreated animals. RNA treatment also accelerated liver regeneration, though not as markedly as DNA-administration.

Certain derivatives of deoxyribonucleosides have been prepared. Casida et al., *Biochemical Pharmacology* vol. 15, p. 627–644, 1966, describe the preparation of the 3'5'-diacetyl, dipropionyl and dibutyryl esters of 2'-deoxythymidine. Rosowsky et al., *Cancer Treatment Reports* vol. 65 No.1–2, p. 93–99, January/February 1981, and Ensminger et al., *Biochemical Pharmacology* vol. 28, p. 1541–1545, October 1978, describe the use of thymidine 5'-O-pivaloate to supply thymidine to tissues.

Since the primary determinant of recovery or survival after exposure to ionizing radiation or chemical mutagens is the preservation or repair of DNA, a number of compounds have been found which, when present in an organism at the time of exposure to radiation or chemical mutagens, attenuate the damage to DNA and other cellular structures. Included in this class of compounds are antioxidants, sulfhydryl compounds, and the enzymes superoxide dismutase and catalase. However, these compounds have been found to be only moderately protective or practical to use in vivo, in part because they can be toxic in effective concentrations. Since these compounds must be present in the organism at the time of exposure to radiation or chemical mutagens, they are obviously not useful in the case of unexpected or accidental exposure.

Reportedly, sulfhydryl compounds are the most effective radioprotective agents known. Examples of these compounds include mercaptoethylamine (MEA), 2-β-aminoethyl-isothiouronium-Br—HBr (AET), 5-hydroxytryptamine (HT), and 5-2-(3-amino-propylamino) ethylphosphorothiotoic acid (WR-2721). However, many of these compounds are toxic. Thus, several investigators have attempted to increase protection against radiation damage and to decrease toxicity by using mixtures of these chemical protectors. The results of these studies demonstrate that the administration of mixtures of radioprotectors not only increases the degree of protection for short and long term survival compared with that from each substance given separately, but also diminishes the toxicity of compounds such as AET or MEA. Administration of sulfhydryl chemical radioprotectors before exposure to radiation diminishes markedly the changes induced by radiation in the structures. Maisin, J. R., in: *Symposium on Perspectives in Radioprotection*, Armed Forces Radiobiology Research Institute, Bethesda, Md., p. 53 (1987).

Thiols reportedly protect DNA by mechanisms comprising hydroxyl radical scavenging and DNA radical repair mechanisms. Thus, the extent of interactions of thiols with DNA determines the amount of protection. Cationic thiols (2-[(aminopropyl)amino]ethanethiol (WR-1065) and cysteamine) are better protectors than neutral thiol (2-mercaptoethanol and dithiothreitol) which are in turn better protectors than anionic thiols (glutathione (GSH), 2-mercaptoethanesulfonic acid, and mercaptosuccinate). Such differential binding provides a basis for understanding why WR-1065, which scavenges hydroxyl radicals at a rate comparable to that for GSH, effectively protects cells at concentrations well below those of GSH. Fahery, R. C., *ibid.*, p. 31.

In studies of Chinese hamster V-79 cells treated with gamma radiation and with bromodeoxyuridine (BrdUrd) and light photolysis were compared. When treated with gamma radiation, WR-2721 was found to improve cell survival both by acting as a reducer of gamma radiation, and by causing increase in DNA repair and increase in rejoining of DNA strand breaks. Cysteamine has been shown to act as a reducer of gamma radiation damage without affecting the rejoining of strand breaks or DNA repair capacity. Nicotinamide (NA) has been shown to directly affect DNA repair through the polyADPribose system which is activated by DNA single strand breaks, thus providing NA concentration dependent protection or sensitization. These compounds exhibit a different effect on cells treated with BrdUrd and light compared with gamma radiation. WR-2721 does not reduce strand break formation. MEA and NA reduce damage formation by about 30%. WR-2721 did not affect the rejoining of BrdUrd/light-induced DNA strand breaks. Only NA increased the repair capability of cells subjected to DrdUrd and light damage. Prager, A., et al., *ibid.*, p. 43.

In addition to the use of-thiols, radioprotection has been achieved with "biological response modifiers" (BRM), either alone or in combination with other agents. Such biological response modifiers include glucan, OK-432, Biostim, PSK, Lentinan, Schizophyllan, Rhodexman, Levan, Mannozym, and MVE-2. Of these BRM's, glucan was found to be the most radioprotective. Glucan is a beta 1–3 polyglycan isolated from the yeast *Saccharomyces cerevisiae*. Glucan's radioprotective capacity is attributed to its ability both to protect and/or enhance recovery of hemoatopoietic stem cell populations, and to enhance or maintain the function of macrophage cell populations important in combatting otherwise lethal post-irradiation opportunistic infections. The combination of glucan and WR-2721 resulted in both additive and synergistic radioprotective effects. Patchen, M. L., *ibid.*, P. 68.

Other polysaccharides have also been found to be radioprotective. Intravenous administration of the polysaccharide extracted from the yeast *Rhodotorula rubra*, mannane mannozyme (MMZ), and the particulate polyglucans GLP/B04 and GLP/B05 (unbranched glucans with alternating B-1,3 and B-1,6 bonds), significantly decreased the mortality of mice exposed to a single dose of X-rays. Maisin, J. R., *ibid.*, p. 69.

The cytokines IL-2 and TNF have also been found to be effective radioprotective compounds. Cytokines are released upon administration of numerous inflammatory agents. Many of these inflammatory agents stimulate the reticuloendothelial system and are radioprotective. Neta, R., *ibid.*, p. 71.

Thymic peptides, such as thymic factor TP-5, have also been reported to reverse or greatly ameliorate immune depression due to limited portal irradiation of thymus, circulating blood, and lymphoid tissues. The immune restorative effect of thymic factors is due to their maturational effect on bone marrow immunocyte precursors. Chretien, P. B., *ibid.*, p. 72.

The antioxidant enzymes glutathione peroxidase (GSH-Px), superoxide dismutase (SOD), catalase, glutathione reductase and glutathione transferase scavenge free radical species produced by radiation and/or the products of free radical cellular damage, and thus play a role in radioprotection. GSH-Px exhibits and best correlation between enzyme activity and cell radiosensitivity. Administration of enzyme preparations or drugs or chemicals which mimic or activate or induce these enzymes may enhance radioprotection. The radioprotectors MEA, WR-2721 and diethyldithiocarbamate (DDC) enhance mouse liver GSH-Px activity 1 to 2 hours after administration. Selenium and selenium-containing compounds also exhibit a small radioprotective effect. The levels of GSH-Px in mouse bone marrow were found to increase 30% 24 hours after administration of selenium. When selenium was administered before WR-2721, a decrease in toxicity and an increase in radioprotection was observed. Superoxide dismutase (SOD) and catalase were also observed to increase upon administration of selenium. In addition, metal ions and metal-containing compounds which mimic antioxidant enzymes may also act as radioprotectors. Copper and zinc metal ions in SOD are marginally radioprotective. Mimetics of SOD include bis (3,5-diisopropylsalicylato) copper and the bivalent copper complex of 3-mercapto-2-hydroxypropylether of dextran. Dumar, K. S., *ibid.*, p. 89. For a review on SOD, see Fridovich, I., *Annu. Rev. Biochem.* 44: 147–159 (1975).

Induction of metallothionein (MT) in the body by treatment with some heavy metals or immunostimulants has been found to be a potent means for inducing radioprotection. The metal salts $CdCl_2$, $MnCl_2$ or zinc acetate or the immunostimulants OK-432 or IL-1 elevates MT levels in the liver of pretreated mice 10 to 20 times of the control level. The number of leukocytes as well as erythrocytes were reduced temporarily even in pretreated mice. However, the cell counts of pretreated mice showed a faster recovery. Matsubara, J., et al., ibid., p. 99.

Vitamin A and beta carotene have also been suggested as radioprotective agents. They may be involved, in ameliorating the oxidative damage in tissues of irradiated mammals which results from production of free radicals such as hydroxy radicals or $H_2O^+$ and its daughter products. Radiation may also create injury to cell structures either by the direct effect of radiation or by the production of toxic metabolites. Radiation injury results in disturbed extracellular and intracellular oxygen levels and perturbed intracellular electron transport and metabolism. Oxidative damage may be enhanced by sudden elevations of local oxygen levels caused by reperfusion of tissues after radiation-induced vasoconstriction or by reversal of radiation-induced bronchoconstriction. Damage occurs where local oxygen levels are in excess of what the tissues can consume. Vitamin A and beta carotene were found to exhibit protective action in rodents exposed to whole body and local radiation. Seifter, E., et al., ibid. p. 104.

Prostaglandins and related compounds of the arachidonic acid cascade protect cells in vivo from some degree of ionizing radiation injury. Among the array of physiological actions of prostaglandins is the protection of cells and tissues from a variety of injuries including strong acids, bases, and absolute ethanol. Prostaglandins were found to exhibit maximal protection at levels a thousandfold lower than those needed for WR-2721. Hanson, W. R., ibid., p. 105.

Methylene blue, a compound used clinically as an anti-inflammatory, antimalarial, and antibacterial agent as well as in the treatment of carbon monoxide poisoning and as an antidote for cyanide poisoning, as also found to protect the intestinal mucosa of rats subjected to sublethal radiation-induced damage. Irradiation damages tissues through the production of highly bioactive free radical species. Therefore, it was hypothesized that methylene blue would also protect irradiated rats from free-radical mediated tissue damage. Scheving, L. E., et al., ibid., p. 115.

In addition, N-arylacetyldehydroalanines reportedly inhibit superoxide anion and hydroxyl free radical-mediated processes, thereby providing radioprotective activity. Buc-Calderone, P., et al., ibid., p. 116.

OBJECTS OF THE INVENTION

While the strategy of delivering DNA and/or deoxyribonucleosides to physiologically or pathologically damaged tissue has been recognized, the art has heretofore failed to provide satisfactory methods for introducing deoxyribonucleosides in sufficiently high and reliable amounts to successfully treat the pathological and physiological conditions and to promote cellular repair and survival of the animal. Moreover, although a variety of compounds have been developed which protect animals against some effects of ionizing radiation or chemical mutagens, deoxyribonucleosides provided to tissues for a sufficient time have the greatest clinical potential for post-exposure treatment of such damage. Clinical implementation of this strategy, however, awaits development of satisfactory and convenient methods for delivering adequate quantities of deoxyribunucleosides to tissues in vivo. Similarly, full appreciation and clinical implementation of the capacity of deoxyribonucleosides to promote wound healing or tissue repair awaits development of satisfactory methods for their delivery to tissues in vivo.

It is thus a primary object of this invention to identify pharmaceutically acceptable compounds which can efficiently be used to deliver pharmacologically effective amounts of deoxyribonucleosides or their respective derivatives to animal tissue.

It is still a further object of this invention to provide a family of deoxyribonucleoside derivatives which can be effectively administered orally or parenterally, which have no undesirable toxic effects, and which can be administered to animals and humans to effectively promote cellular repair in a number of physiological and pathological conditions and to promote survival of the animal when administered after exposure to radiation has occurred.

It is still a further and related object of this invention to provide certain derivatives of 2'-deoxyadenosine, 2'-deoxyguanosine, 2'-deoxycytidine, and 2'-deoxythymidine which, when administered to an animal, enhance the bioavailability of those deoxyribonucleosides to the animal tissue.

It is a related object of this invention to substantially improve the bioavailability of 2'-deoxyadenosine, 2'-deoxyguanosine, 2'-deoxycytidine, and 2'-deoxythymidine by enhancing the transport of these deoxyribonucleosides across the gastrointestinal tract, the blood-brain barrier, and other biological membranes.

It is still a further and more specific object of this invention to provide a family of deoxyribonucleoside derivatives for the treatment of a variety of heart, muscle, liver, bone, skin, and other pathological and physiological conditions.

It is still a further object of this invention to provide deoxyribonucleoside derivatives and methods for using those derivatives which are safe, inexpensive, and which accelerate the normal cellular processes of regeneration and healing.

SUMMARY OF THE INVENTION

These and other objects of the invention are achieved by the administration of certain acyl derivatives of 2'-deoxyadenosine, 2'-deoxyguanosine, 2'-deoxycytidine, and 2'-deoxythymidine. These acyl derivatives can be used to prevent or treat radiation, sunlight and mutagen-induced cellular damage, to improve the healing of wounds, or repair damaged tissues, and in the treatment of other physiological and pathological tissue conditions.

Broadly, the acyl derivatives of 2'-deoxyadenosine are those having the formula

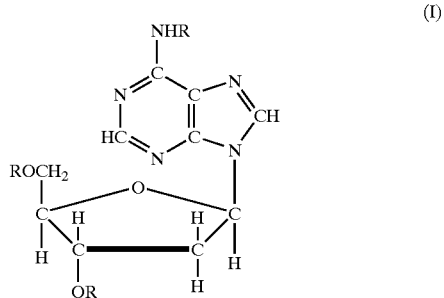

(I)

wherein R is hydrogen or an acyl radical of a metabolite other than acetyl, with the proviso that at least one R is not hydrogen, or the pharmaceutically acceptable salt thereof.

The preferred acyl derivatives of 2'-deoxyadenosine are those having the formula

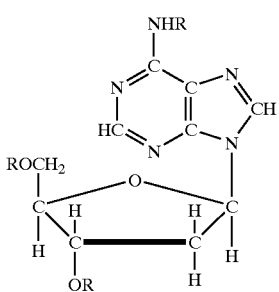

(I)

where R is H or an acyl group derived from a carboxylic acid selected from one or more of the group consisting of pyruvic acid, lactic acid, enolpyruvic acid, an amino acid, a fatty acid other than acetic acid, lipoic acid, nicotinic acid, pantothenic acid, succinic acid, fumaric acid, p-aminobenzoic acid, betahydroxybutyric acid, orotic acid, and carnitine, with the proviso that at least one R is not hydrogen, or the pharmaceutically acceptable salt thereof.

Broadly, the acyl derivatives of 2'-deoxyguanosine are those having the formula

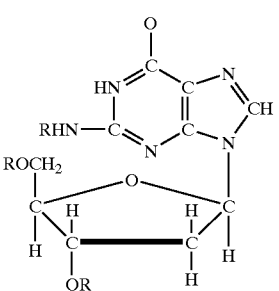

(II)

wherein R is hydrogen or an acyl radical of a metabolite other than acetyl, with the proviso that at least one R is not hydrogen, or the pharmaceutically acceptable salt thereof.

The preferred acyl derivatives of 2'-deoxyguanosine are those having the formula

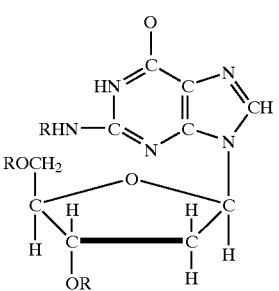

(II)

wherein R is H or an acyl group derived from a carboxylic acid selected from one or more of the group consisting of pyruvic acid, lactic acid, enolpyruvic acid, an amino acid, a fatty acid other than acetic acid, lipoic acid, nicotinic acid, pantothenic acid, succinic acid, fumaric acid, p-aminobenzoic acid, betahydroxybutyric acid, orotic acid, and carnitine, with the proviso that at least one R is not hydrogen, or the pharmaceutically acceptable salt thereof.

Broadly, the acyl derivatives of 2'-deoxycytidine are those having the formula

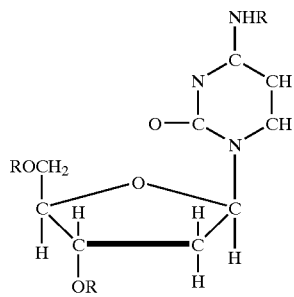

(III)

wherein R is hydrogen or an acyl radical of a metabolite other than acetyl, with the proviso that at least one R is not hydrogen, or the pharmaceutically acceptable salt thereof.

The preferred acyl derivatives of 2'-deoxycytidine are those having the formula

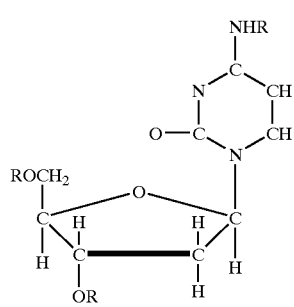

(III)

wherein R is H or an acyl group derived from a carboxylic acid selected from one or more of the group consisting of pyruvic acid, lactic acid, enolpyruvic acid, an amino acid, a fatty acid other than acetic acid, lipoic acid, nicotinic acid, pantothenic acid, succinic acid, fumaric acid, p-aminobenzoic acid, betahydroxybutyric acid, orotic acid, and carnitine, with the proviso that at least one R is not hydrogen, or the pharmaceutically acceptable salt thereof.

Broadly, the acyl derivatives of 2'-deoxythymidine are those having the formula

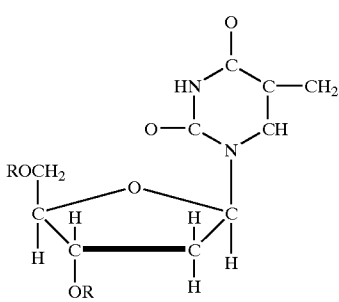

(IV)

wherein R is hydrogen or an acyl radical of a metabolite other than a fatty acid having less than five carbon atoms, with the proviso that at least one R is not hydrogen, or the pharmaceutically acceptable salt thereof.

The preferred acyl derivatives of 2'-deoxythymidine are those having the formula

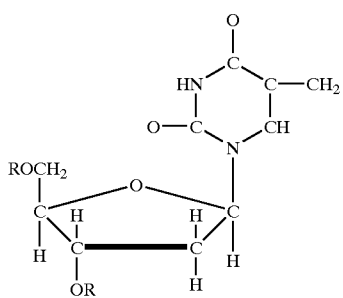

(IV)

wherein R is B or an acyl group derived from a carboxylic acid selected from one or more of the group consisting of pyruvic acid, lactic acid, enolpyruvic acid, an amino acid, a fatty acid containing 5 or more carbon atoms, lipoic acid, nicotinic acid, pantothenic acid, succinic acid, fumaric acid, p-aminobenzoic acid, betahydroxybutyric acid, orotic acid and carnitine, with the proviso that at least one R substituent is not hydrogen, or the pharmaceutically acceptable salt thereof.

The acyl derivatives of 2'-deoxythymidine may also be those having the formula

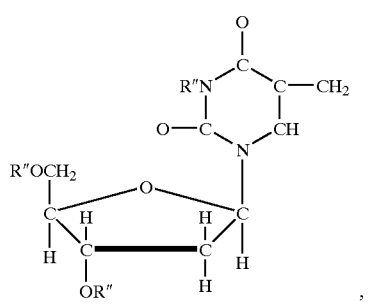

(V)

wherein R" is hydrogen or an acyl radical of a metabolite, with the proviso that the R" on nitrogen is not hydrogen, or the pharmaceutically acceptable salt thereof.

Preferred acyl derivatives of 2'-deoxythymidine are those having the formula

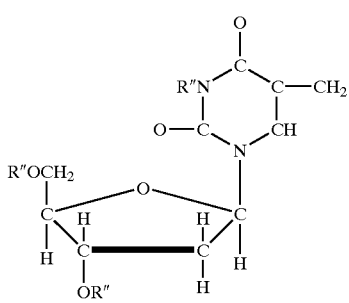

(V)

wherein R" is H or an acyl group derived from a carboxylic acid selected from one or more of the group consisting of pyruvic acid, lactic acid, enolpyruvic acid, an amino acid, a fatty acid, lipoic acid, nicotinic acid, pantothenic acid, succinic acid, fumaric acid, p-aminobenzoic acid, betahydroxybutyric acid, orotic acid, and carnitine, with the proviso that the R" on nitrogen is not hydrogen, or the pharmaceutically salt thereof.

The invention also includes compounds having formulae I–IV wherein the ribose moiety is monoacylated at the 3' or 5' position with the derivative of a fatty acid and includes 3',5' diacylated derivatives of compounds I–IV wherein at least one such substituent is derived from a fatty acid having 5 or more carbon atoms.

The acyl derivatives of 2'-deoxyadenosine, 2'-deoxyguanosine, 2'-deoxycytidine, and 2'-deoxythymidine having formulae I, II, III, and V, desirably are substituted with an acyl derivative of a carboxylic acid having 3–22 carbon atoms.

Where acyl derivatives of any of the compounds of formulae I–V are substituted by an acyl group derived from an amino acid, the amino acid is desirably selected from the group consisting of glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, and hydroxylysine.

In a preferred embodiment of the invention, a mixture of at least two acyl derivatives of 2'-deoxyadenosine, 2'-deoxyguanosine, 2'-deoxycytidine, and 2'-deoxythymidine is used. Said compositions contain at least two of the acyl derivatives having the formulae

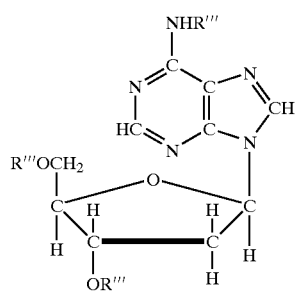

(I)

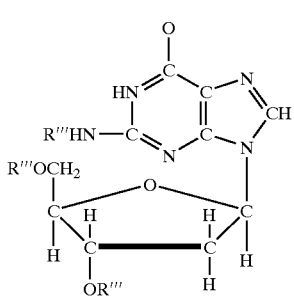

(II)

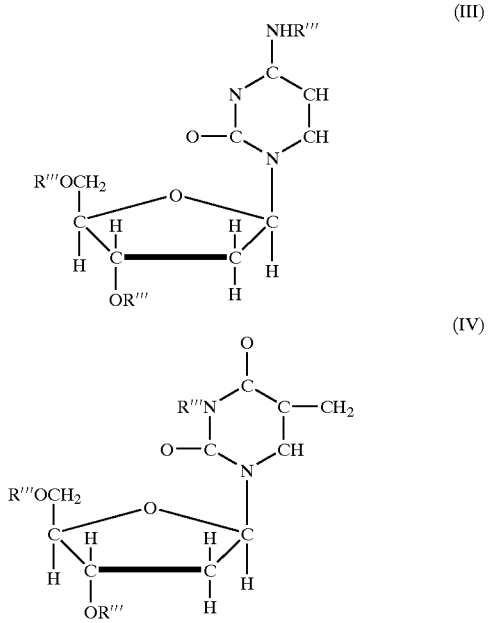

wherein R''' is H or an acyl group derived from a carboxylic acid selected from one or more of the group consisting of pyruvic acid, lactic acid, enolpyruvic acid, an amino acid, a fatty acid, lipoic acid, nicotinic acid, pantothenic acid, succinic acid, fumaric acid, p-aminobenzoic acid, betahydroxybutyric acid, orotic acid, and carnitine, with the proviso that at least one R is not hydrogen, or the pharmaceutically acceptable salt thereof.

Further substantial benefits may be obtained, particularly where the compositions of the invention are used to ameliorate the effects of radiation, if a radioprotective compound is included together with one or more of the acyl deoxyribonucleosides. The radioprotective compounds may be those selected from the group consisting of WR-2721, NAC, DDC, cysteamine, 2-mercaptoethanol, mercaptoethylamine dithiothreitol, glutathione, 2-mercaptoethanesulfonic acid, WR-1065, nicotinamine, 5-hydroxytryptamine, 2-aminoethyl-isothiouronium-Br—Hbr, glucans, GLP/B04, GLP/B05, OK-432, Biostim, PSK, Lentinan, Schizophyllan, Rhodexman, Levan, Mannozym, MVE-2, MNR, MMZ, IL-1, TNF, thymic factor TF-5, glutathione peroxidase, superoxide dismutase, catalase, glutathione reductase, glutathione transferase, selenium, $CdCl_2$, $MnCl_2$, Zn acetate, Vitamin A, beta carotene, prostaglandins, tocopherol, methylene blue and PABA.

The invention is also embodied in pharmaceutical compositions which comprise one or more of the novel deoxyribonucleosides together with a pharmaceutically acceptable carrier. In addition, known acetyl derivatives of the 2'-deoxyadenosine, 2'-deoxyguanosine, 2'-deoxycytidine and 2'-deoxythymidine as well as the fatty acid derivatives of thymidine wherein the acyl group contains 3 or 4 carbon atoms may be used alone, in combination with one another or in combination with one or more novel compounds, in pharmaceutical compositions of the invention. The composition may further include a radioprotective compound as described. The compositions may be in the form of a liquid, a suspension, a tablet, a dragee, an injectable solution, a topical solution, or a suppository.

A skin lotion may be advantageously prepared by combining an effective amount of one or more of the acyl deoxyribonucleosides of the invention together with a suitable carrier. Such a skin lotion advantageously contains from 0.1 to 5 percent by weight of the deoxyribonucleosides and, if desirable, the radioprotective compound.

The pharmaceutical compositions of the invention can also be embodied in bioerodible microcapsules, the microcapsules desirably being selected from the group consisting of polylactate or lactate-glycolate copolymers.

It is believed that the delivery of exogenous deoxyribonucleosides to the tissue of an animal can be effectively achieved by administering to that animal an effective amount of an acyl derivative of a deoxyribonucleoside of formulae I–V. By enhancing the delivery of exogenous deoxyribonucleosides, and thereby increasing their bioavailability, it may be possible to treat physiological or pathological conditions of the tissues of an animal by essentially supporting the metabolic functions thereof. Without being bound by theory, the invention may work, as well, by increasing the bioavailability of nucleoside anabolites e.g. nucleotides or nucleotide-derived cofactors. Administration of the nucleosides per se increases their bioavailability but, due to rapid catabolism, this may not result in significant elevation of nucleotide levels; i.e., one does not necessarily get an increase in intracellular levels because at lower nucleoside levels there is rapid uptake by the cells whereas at higher levels there is saturation and the excess is degraded. The invention is believed to work by delivering a steady supply of nucleoside at low levels.

It is believed that the novel compounds and compositions of the invention may be used advantageously in methods for treating cardiac insufficiency, myocardial infarction, the consequences of hypertension, cirrhosis of the liver, diabetes, senescence, adrenal insufficiency, the complications of pregnancy, cerebrovascular disorders, senile dementias, Parkinson's disease, demyelinating disorders, cerebellar ataxia, infant respiratory distress syndrome, and lung disorders, or to enhance bone healing or muscle performance.

The specific methods where advantages may be achieved using the compounds and compositions of the invention include treating or preventing radiation-induced cellular damage, preventing sunlight-induced cellular damage, ameliorating the effects of aging, preventing mutagen-induced cellular damage, healing damaged tissue, healing skin wounds, healing burn tissue, healing diseased or damaged liver tissue, healing heart muscle damaged as a result of myocardial infarction, treating damaged bone marrow, and enhancing erythropoiesis. In treating all of these conditions, a compound of the invention, with or without additional carriers, radioprotective compounds, and other adjuvants, are administered to an animal.

The invention essentially enhances the transport of deoxyribonucleosides across biological membranes, including the gastrointestinal tract (i.e., transport from the gut into the bloodstream) and the blood-brain barrier. The rapid catabolism by nucleoside phosphorylases or nucleoside deaminases is also substantially prevented.

Administration of the acylated derivatives offers certain advantages over the nonderivatized compounds. The acyl substituents can be selected to increase the lipophilicity of the nucleoside, thus improving its transport from the gastrointestinal tract into the bloodstream. The acylated derivatives are effective when administered orally. The acylated derivatives are resistant to catabolism by nucleoside deaminases and nucleoside phosphorylases in the intestine, liver, other organs, and the bloodstream. Thus, administration of the acylated derivatives of the invention, either orally or parenterally, allows sustained delivery of high levels of deoxyribonucleosides to the tissues of an animal.

DESCRIPTION OF THE DRAWINGS

FIG. 1 is a graph illustrating the rates of degradation of deoxyribonucleosides in plasma. The following abbreviations were used:

dT=2'-Deoxythymidine
dC=2'-Deoxycytidine
dG=2'-Deoxyguanosine
dA=2'-Deoxyadenosine.

FIG. 2 is a graph illustrating the disappearance of deoxyadenosine derivatives in plasma.

FIG. 3 is a graph illustrating the disappearance of dexoyadenosine derivatives in liver extract.

DESCRIPTION OF THE PREFERRED EMBODIMENTS

A "metabolite" is a chemical compound that is formed by, or participates in, a metabolic reaction. In the context of this application, metabolites include not only acyl substituents known to be synthesized within the human body, but also naturally occurring (but perhaps synthesized rather than extracted) substituents that might be derived from other animal or plant sources. The limiting criteria are that the compound should be substantially nontoxic and biocompatible, and should readily enter into metabolic pathways in vivo, so as to present essentially no toxicity during long-term consumption in the doses proposed. It is preferable that the substituents be metabolized rather than excreted intact (or conjugated through detoxification reactions), as concentration of carboxylic acids within the kidney may lead to undesirable excessive acidity. Therefore, carboxylic acids that normally or easily participate in intermediary, catabolic, or anabolic metabolism are preferred substituents.

The term "pharmaceutically acceptable salts" means salts with pharmaceutically acceptable acid addition salts of the deoxyribonucleoside derivatives, which include, but are not limited to, sulfuric, hydrochloric, or phosphoric acids.

The term "coadministered" means that at least two of the acylated derivatives of the invention are administered during a time frame wherein the respective periods of pharmacological activity overlap.

"Acyl derivatives" means derivatives of a 2'-deoxyribonucleoside in which a substantially nontoxic organic acyl substituent derived from a carboxylic acid is attached to one or more of the free hydroxyl groups of the ribose moiety of the deoxyribonucleoside with an ester linkage and/or where such a substituent is attached to a primary or secondary amine in the pyrimidine ring of deoxycytidine or deoxythymidine, or in the purine ring of deoxyadenosine or deoxyguanosine, with an amide linkage. Such acyl substituents are derived from carboxylic acids which include, but are not limited to, compounds from the group consisting of pyruvic acid, lactic acid, enolpyruvic acid, an amino acid, a fatty acid, lipoic acid, nicotinic acid, pantothenic acid, succinic acid, fumaric acid, p-aminobenzoic acid, betahydroxybutyric acid, orotic acid, and carnitinic acid. Preferred acyl substituents are compounds which are normally present in the body, either as dietary constituents or as intermediary metabolites, which are, essentially nontoxic when cleaved from the deoxyribonucleoside in vivo.

"Amino acids" include, but are not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, and other naturally occuring amino acids.

"Fatty acids" are carboxylic acids-having 2–22 carbon atoms. Such fatty acids may be saturated, partially saturated or polyunsaturated.

Preferred acyl derivatives of 2-deoxyribonucleosides for enhancing transport across biological membranes are those which are more lipophilic than are the parent nucleosides. In general, lipophilic acyl nucleoside derivatives have acyl substituents which are nonpolar (aside from the carboxylate group). Lipophilic acyl substituents include, but are not limited to, groups derived from acetic acid, lipoic acid, and fatty acids. One of ordinary skill in the art can determine whether a particular acyl-substituted nucleoside derivative is more lipophilic than the underivatized nucleoside using standard techniques, i.e., comparison of the partition coefficients determined in water-octanol mixtures.

Following passage of the acylated nucleoside derivative from the gastrointestinal tract into the bloodstream, across the blood-brain barrier, or across other biological membranes, the acyl substituents are cleaved by plasma and tissue esterases (or amidases) to give the free nucleosides. The preferred acyl groups of the invention are naturally occurring metabolites in the body, or are compounds which readily enter intermediary metabolic pathways. Thus they offer little toxicity when released in vivo by endogenous esterases or amidases.

The rate of removal of the acyl substituents in vivo is a function of the specificity of plasma and tissue deacylating enzymes (primarily esterases or amidases). Fatty acid substituents containing 4 to 8 carbon atoms are cleaved much more rapidly in vivo than are fatty acids with either more or fewer carbon atoms. Acyl substituents attached to an amine group in the pyrimidine ring of deoxycytidine or deoxythymidine, or the purine ring of deoxyadenosine or deoxyguanosine, with an amide linkage are cleaved more slowly than are substituents attached to hydroxl groups of ribose with an ester linkage.

It is also possible to prepare acyl nucleoside derivatives which contain both polar and nonpolar acyl substituents. The polar acyl group will retard passage of the nucleoside derivative from the gastrointestinal tract, allowing for a more sustained delivery of the compound into the bloodstream after a single dose. The polar group may be cleaved by esterases, amidases, or peptidases present in the intestinal tract to give a nucleoside with a nonpolar acyl substituent which may then efficiently enter the circulation. Polar acyl substituents may be chosen by one of ordinary skill in the art, without undue experimentation, which are cleaved at a slower rate than are nonpolar acyl substituents.

The acyl derivatives are also less susceptible to degradation of the nucleoside moiety by enzymes in plasma and non-target tissues, and are also less susceptible to elimination from the bloodstream via the kidneys. For parenteral injection, acyl derivatives with polar substituents, which are therefore water soluble yet resistant to premature degradation or elimination, may be used with advantage. Preferred acyl substituents for such applications include those derived from glycolic and lactic acids and from amino acids with polar side chains.

Therapeutic Uses

The lipophilic acyl deoxyribonucleoside derivatives of the invention are useful for enhancing the transport of the deoxyribonucleosides across biological membranes including the gastrointestinal tract and blood-brain barrier in animals and thereby increase the bioavailability of the deoxyribonucleosides. Foremost among such animals are humans; however, the invention is not intended to be so limiting, it being within the contemplation of the invention to treat all animals which may experience a beneficial effect from the administration of the acyl deoxyribonucleosides of the invention.

The compositions of the present invention may be administered to an animal either before or after exposure to radiation, sunlight or mutagens. The acyl derivative form of the deoxyribonucleosides provides an orally effective means for delivery of deoxyribonucleosides to tissues. These derivatives may also be given parenterally. Administration of the derivatives avoids the problem of rapid catabolism by gastrointestinal, liver and plasma enzymes.

As shown in FIG. 1, free deoxyguanosine (dG) and deoxyadenosine (dA) are degraded in plasma at a much higher rate than deoxythymidine (dT) and deoxycytidine (dC). Thus, the compositions of the invention may include levels of dG and dA which are higher than the levels of dT and dC to compensate for this differential rate of degradation.

Acyl substituents for derivatization of dA and dG may be selected which are slowly cleaved by esterases so that a prolonged bioavailability of these deoxyribonucleosides may be maintained. Since dT and dC are more slowly degraded, an acyl substituent which is more rapidly cleaved may be used.

The fates of deoxyadenosine, N4-acetyldeoxyadenosine, and N4-valeryldeoxyadenosine in plasma are shown in FIG. 2. Each of these compounds was added to separate aliquots of rat plasma, at initial concentrations of 20 micromolar. The plasma was sampled at various time points, and the desired compounds were assayed by liquid chromatography.

Deoxyadenosine (dA) is very rapidly degraded in plasma, disappearing within 10 minutes. Administration of this compound to an animal or human subject would make deoxyadenosine available to tissues for a very short period of time.

N4-acetyldeoxyadenosine and N4-valeryldeoxyadenosine are, however, deacylated in plasma (to form deoxyadenosine) over a period of several hours. Therefore, administration of either of these compounds would result in prolonged availability of deoxyadenosine to tissues.

The fates of deoxyadenosine, N4-acetyldeoxyadenosine, and N4-valeryldeoxyadenosine in liver extract are shown in FIG. 3. Each of these compounds was added to separate aliquots of an aqueous extract of rat liver, at initial concentrations of 20 micromolar. The extract was sampled at various time points, and the desired compounds were assayed by liquid chromatography.

Deoxyadenosine (dA) is extremely rapidly degraded in plasma, disappearing within 1 minute. The initial degradation product is deoxyinosine, which is not directly reutilizable by tissues. Administration of deoxyadenosine per se to an animal or human subject would make deoxyadenosine available to tissues for only a very short period of time.

N4-acetyldeoxyadenosine and N4-valeryldeoxyadenosine are, however, deacylated in liver extract (to form deoxyadenosine) over a period of more than 1 hour. Therefore, administration of either of these compounds would result in prolonged availability of deoxyadenosine to liver or other organs.

Thus a mixture of several different acyl derivatives of each deoxyribonucleoside in an administered dose may be selected to provide optimal bioavailability. A composition containing 3',5'-diacetyl-2'-deoxycytidine, 5'-palmitoyl-2'-deoxycytidine, and $N^4$-palmitoyl-2'-deoxycytidine (and corresponding derivatives of other deoxyribonucleosides) provides a more prolonged bioavailability of nucleosides after a single dose than does an administration of a single acyl derivative of each nucleoside. Thus, after administration of the mixture described above, the acetylated compound is relatively rapidly deacetylated yielding free deoxycytidine (or other desired deoxyribonucleosides) shortly after administration. The 5'-palmitoyl derivative is deacylated more slowly, providing additional free deoxycytidine after the deoxycytidine derived from 3',5'-diacetyl-2'-deoxycytidine has been metabolized by tissues. The $N^4$-palmitoyl derivative is deacylated still more slowly than is 5'-palmitoyl-2'-deoxycytidine.

The acyl deoxyribonucleoside compositions of the invention also find use in treatment of ultraviolet light-induced cellular damage that occurs upon exposure to sunlight. Within 72 hours after exposure to sunlight, there is an increase in the number of epidermal cells and a high rate of mitotic activity. The rate of cell proliferation decreases after 7 to 10 days and the thickness of the epidermis gradually returns to normal within the next 30 to 60 days. Damage to DNA by sunburn-producing UV light (290–320 nm) may result in mutation or cell death. The principal photoproducts are pyrimidine dimers (e.g., thymine dimers). Cell membranes, DNA, RNA, protein and other molecules may be altered, and the synthesis of DNA, RNA and protein may be temporarily inhibited immediately after irradiation. New synthesis is evident by 24 hours and is maximal by 60 hours. Harrison's *Principles of Internal Medicine*, Petersdorf et al., eds., 10th Edition, McGraw-Hill Book Company, New York, N.Y., p. 276 (1983). Thus, administration of the acyl deoxyribonucleosides of the invention provides optimal levels of deoxyribonucleosides during the period of DNA repair after sunlight exposure to ensure maximal cellular protection and repair.

The acyl deoxyribonucleoside composition may be formulated as part of a suntan lotion that may be applied before or after exposure to sunlight. The suntan lotion may also comprise one or more sun blockers such as PABA, esters of PABA, and other non-PABA chemical sunscreens. See Harrison, *supra*, p. 279. The acyl deoxynucleotides are absorbed by the skin and taken up by cells. The acyl deoxyribonucleosides are then cleaved by tissue esterases to give free deoxyribonucleosides in amounts effective for repair of sunlight-induced chromosomal damage. The combination of the acyl deoxyribonucleoside compositions and a sun blocker such as PABA offers maximal protection of the skin from the sun.

The acyl deoxyribonucleoside compositions of the invention also find use in ameliorating the effects of aging by providing a high and sustained level of deoxyribonucleosides to enhance the natural DNA repair processes of cells, and thereby, treating the naturally occurring progressive accumulation of damage to DNA which occurs on aging. Compositions for treatment or amelioration of the effects of aging may be applied topically, in the form of a skin lotion, or may be administered orally or parenterally.

There are conditions other than radiation damage in which exogenous deoxyribonucleosides or derivatives thereof have useful therapeutic applications. Deoxyribonucleic acid has been used to accelerate wound cicatrization or healing, and also to accelerate liver regeneration in experimental animals. It is likely that in these situations, as well as in the situations where DNA is used to promote survival after irradiation of animals, the DNA is serving as a storage depot for deoxyribonucleosides, which gradually releases the deoxyribonucleotides and deoxyribonucleosides during enzymatic degradation.

Administration of acylated deoxyribonucleosides, as described herein, is a method for delivering deoxyribonucleosides to tissues which is preferable to the administration of foreign DNA for the purpose of improving wound healing or tissue regeneration. Unlike DNA, acylated deoxyribonucleosides are effective after oral administration; they are also nonantigenic and are much easier to purify than DNA.

The composition of the present invention may also be administered to enhance the healing of damaged tissue. Such damaged tissue includes skin wounds (e.g., punctures, lacerations, abrasions, etc.), burned tissue (skin, etc.), diseased or damaged liver (from surgery or other wounds of the liver, or from cirrhosis or diabetes, etc.), damaged heart muscle (e.g., from myocardial infarction), and damaged bone marrow (e.g., after radiation treatment or chemotherapeutic treatment).

For the purpose of treating-skin wounds or burns, the compositions may be applied topically as part of a skin lotion or cream, or as part of a bioerodible polymer.

Preferred acyl substituent groups of 2'-deoxyadenosine, 2'-deoxyguanosine, 2'-deoxycytidine, and 2'-deoxythymidine are those which form the acetate, valerate and palmitate esters.

Preferred deoxyadenosine derivatives comprise $N^6$-palmitoyl-3',5'-diacetyl-2'-deoxyadenosine, N6-palmitoyl-5'-valeryl-2'-deoxyadenosine, and 5'-valeryl-2'-deoxyadenosine.

Preferred deoxyguanosine derivatives comprise $N^2$-palmitoyl-3',5'-diacetyl-2'-deoxyguanosine, and 5'-palmitoyl-2'-deoxyadenosine.

Preferred deoxycytidine derivatives comprise $N^4$-palmitoyl-2'-deoxycytidine, 5'-palmitoyl-2'-deoxycytidine, $N^4$-palmitoyl-3',5'-diacetyl-2'-deoxycytidine, and 3',5'-dipalmitoyl-2'-deoxycytidine.

Preferred deoxythymidine derivatives comprise 5'-palmitoyl-2-deoxythymidine and $N^3$-palmitoyl-3',5'-diacetyl-2-deoxythymidine.

Compositions within the scope of the invention include those which contain mixtures of the acyl derivatives of the deoxyribonucleosides in amounts effective to achieve its intended purpose. Such compositions may contain 0 to 50 mole percent of the acyl derivative of deoxycytidine, 0 to 50 mole percent of the acyl derivative of deoxyguanosine, 0 to 50 mole percent of the acyl derivative of deoxythymidine and 0 to 50 mole percent of the acyl derivative of deoxyadenosine, with the proviso that the total content of the acyl deoxyribonucleosides adds up to 100 mole percent.

A preferred composition contains 25 mole percent of the acyl derivative of deoxycytidine, 25 mole percent of the acyl derivative of deoxyguanosine, 25 mole percent of the acyl derivative of deoxythymidine, and 25 mole percent of the acyl derivative of deoxyadenosine.

For treatment of radiation-induced cellular damage, sunburn, or to enhance wound healing, preferred dosages include amounts of the acyl derivatives equivalent to 10 to 1000 mg of 2'-deoxyadenosine, 10 to 1000 mg of 2'-deoxyguanosine, 10 to 1000 mg of 2'-deoxycytidine and 10 to 1000 mg of 2'-deoxythymidine. For example, the composition may comprise 13–1330 mg of 3',5'-diacetyl-2'-deoxyadenosine, 13–1310 mg of 3',3'-diacetyl-2'-deoxyguanosine, 14–1370 mg of 3',5'-diacetyl-2'-deoxycytidine and 14–1350 mg of 3',5'-diacetyl-2'-deoxythymidine. As is understood in the art, in calculating such dosages, the equivalent amount of the 2'-deoxyribnucleoside alone is considered, i.e., the acyl substituent and acid addition portion of any pharmaceutically acceptable salt are not included in the calculation.

For a suntan lotion, 0.1 to 5% by weight of the above compositions may be added. Generally, for this purpose, the acyl derivative will be in the form of the free acyl deoxyribonucleosides and not as the pharmaceutically acceptable salts.

Methods of Preparation

When the acid source of the desired acyl derivative has groups which interfere with the acylation reactions, e.g., hydroxyl or amino groups, these groups may be blocked with protecting groups, e.g., t-butyldimethylsilyl ethers or t-BOC groups, respectively, before preparation of the anhydride. For example, lactic acid may be converted to 2-t-butyldimethylsiloxypropionic acid with t-butyldimethylchlorosilane, followed by hydrolysis of the resulting silyl ester with aqueous base. The anhydride may be formed by reacting the protected acid with DCC. With amino acids, the N-t-BOC derivative may be prepared, using standard techniques, which is then converted to the anhydride with DCC. With acids containing more than one carboxylate group (e.g., succinic, fumaric, or adipic acid) the acid anhydride of the desired dicarboxylic acid is reacted with a 2'-deoxyribonucleoside in pyridine.

3',5'-Diacyldeoxythymidine may be prepared according to methods disclosed by Nishizawa et al., *Biochem. Pharmacol.* 14:1605 (1965), by treating deoxythymidine with 2.1 equivalents of an acid anhydride of the desired acyl compound in pyridine followed by heating to 80–85° C. for at least one hour. Alternatively, deoxythymidine may be treated with 2.1 equivalents of an acid chloride in pyridine at room temperature (see Example 1).

The 5'-hydroxyl group of deoxythymidine may be selectively acylated with 1 equivalent of the acid anhydride of the desired acyl compound in pyridine, which is heated to 80–85° C., according to Nishazawa, et al. Alternatively, the acid chloride (1 equivalent) may be reacted with deoxythymidine in pyridine and DMF at room temperature according to Baker et al., *J. Med. Chem.* 21:1218 (1978). (See Example 2.)

The 3'-hydroxyl group of deoxythymidine may be selectively acylated by selectively forming the 5'-O-t-butyldimethylsilyl derivative with 1.2 equivalents of t-butyldimethylchlorosilane in DMF containing imidizole, followed by acylation of the 3'-hydroxyl group with the appropriate acid anhydride, and cleavage of the 5'-t-butyldimethyl silyl ether according to Baker et al. (See Example 3.)

3',5-Diacyldeoxycytidine may be prepared according to a method adapted from Gish et al., J. Med. Chem. 14:1159 (1971), by treating deoxycytidine hydrochloride with 2.1 equivalents of the appropriate acid chloride in DMF. (See Example 5.)

The 5'-hydroxy group of deoxycytidine may be selectively acylated by treating deoxycytidine hydrochloride with 1.1 equivalents of the appropriate acid anhydride in DMF. Gish et al. (See Example 6.)

The $N^4$-amino group of deoxycytidine may be selectively acylated by treating deoxycytidine with 1.5 equivalents of the appropriate acid anhydride in pyridine which may contain DMF. Alternatively, deoxycytidine may be treated with 1.5 equivalents of the desired acid anhydride in pyridine and DMF. Another procedure for the selective acylation of the $N^4$-amino group of deoxycytidine involves treatment with an excess of the appropriate acid anhydride in a mixture of water and a water-miscible solvent. (See Example 7.)

3',5',N$^4$-Triacyl-2'-deoxycytidine, where all the acyl groups are the same, may be prepared by treating 2'-deoxycytidine with at least 3 equivalents of an acid chloride or anhydride derived from the desired acyl group, in pyridine. To prepare the triacyl derivatives of deoxycytidine where the N$^4$-acyl group is different from the 3',5'-acyl groups, the desired N$^4$-amino group may be first selectively acylated as described above, followed by acylation of the 3' and 5'-hydroxy groups with the desired acid anhydride. Alternatively, the 3',5'-diacyl derivative may be prepared first, followed by acylation of the N$^4$-amino group. (See Example 8.)

The 3',5'-diacyl derivative of deoxyadenosine may be prepared by treatment with 2.1 equivalents of the appropriate acid chloride in DMF. (Adapted from Gish et al., see Example 9.)

The 5'-hydroxyl group of deoxyadenosine may be selectively acylated by treatment of deoxyadenosine hydrochloride with 1.1 equivalents of the desired acid chloride in DMF. (Adapted from Gish et al., see Example 10.)

The N$^6$-amino group of deoxyadenosine may be selectively acylated by treating deoxyadenosine with the desired acid chloride (1.5 equivalents) in a mixture of pyridine and DMF. Alternatively, deoxyadenosine may be treated with 1.5 equivalents of the desired acid anhydride in pyridine and DMP (adapted from Sasaki et al., *Chem. Pharm. Bull.* 15:894 (1967)). The N$^6$-amino group may also be selectively acylated by treatment of deoxyadenosine with 2 equivalents of an appropriate acid anhydride in a mixture comprising water and a water-miscible solvent (adapted from Akiyama et al., *Chem. Pharm. Bull.* 26:981 (1978)) (See Example 11.)

The 3',5'-hydroxyl groups and the N$^6$-amino group may all be acylated by treatment of deoxyadenosine with at least 4 equivalents of the appropriate acid chloride or acid anhydride in pyridine. (See Example 12.)

Alternatively, the N6-amino group of deoxyadenosine may be first selectively acylated as described above, followed by acylation of the 3' and 5' hydroxy groups. Another approach comprises selective acylation of the 3' and 5'-hydroxy groups of deoxyadenosine as described above, followed by acylation of the N$^6$-amino group. These methods give triacyl derivatives where the N$^6$-acyl group is different from the 3' and 5' acyl groups.

3,5-Diacyl-2'-deoxyguanosine may be prepared by treating deoxyguanosine hydrochloride with 2.1 equivalents of the appropriate acid chloride in DMF. (Adapted from Gish et al., see Example 13.)

The 5'-hydroxyl group of deoxyguanosine may be selectively acylated by treatment of deoxyguanosine hydrochloride with 1.1 equivalents of the appropriate acid chloride in DMF. (Adapted from Gish et al., see Example 14.)

The N$^2$-amine of the purine ring of deoxyguanosine may be selectively acylated by treating deoxyguanosine with 1.5 equivalents of the appropriate acid anhydride in pyridine or a mixture of pyridine and DMF (adapted from Sasaki et al., *Chem. Pharm. Bull.* 15:894 (1967). Alternatively, deoxyguanosine may be treated with a twofold excess of the appropriate acid anhydride in a mixture of water and a water-miscible solvent (adapted from Akiyama et al., see Example 15).

3',5',N$^2$-triacyldeoxyguanosine, where all the acyl groups are the same, may be prepared by treating deoxyguanosine with 4 equivalents of the appropriate acid chloride or acid anhydride in pyridine. (See Example 16.)

To prepare the triacyl derivative of deoxyguanosine where the N$^2$-acyl group is different than the 3' and 5' acyl groups, the N$^2$-acyl group may be selectively acylated as described above, followed by acylation of the 3' and 5' hydroxyl groups. Alternatively, the 3' and 5' hydroxyl groups may be acylated first, followed by acylation of the N$^2$-amino group.

These acyl compositions may be administered chronically to an animal which is at risk of either exposure to radiation, sunlight or chemical mutagens. The acyl compositions of the invention may also be administered after exposure to radiation, sunlight or chemical mutagens or after a wound is inflicted to enhance the repair of DNA and thereby to ameliorate the damage and promote survival of the animal. Advantageously, the compositions of the invention may be administered before or after radiotherapy or chemotherapy to ameliorate undesired side effects of the treatment.

The acyl compositions of the invention may also be coadministered with other radioprotective compounds such as WR-2721, NAC, DDC, cysteamine, 2 mercaptoethanol, mercaptoethylamine, dithiothreitol, glutathione, 2-mercaptoethanesulfonic acid, WR-1065, nicotinamide, 5-hydroxytryptamine, 2-2-aminoethyl-isothiouronium-Br—Hbr, glucans, GLP/BO4, GLP/BO5, OK-432, Biostim, PSK, Lentinan, Schizophyllan, Rhodexman, Levan, Mannozym, MVE-2, MNR, MMZ, IL-2, TNF, thymic factor TF-5, glutathione peroxidase, superoxide dismutase, catalase, glutathione reductase, glutathione transferase, selenium, CdCl$_2$, MrCl$_2$, Zn acetate, vitamin A, beta carotene, prostaglandins, tocopherol, and methylene blue. The administration of these protective compounds along with the acyl derivatives of the invention provides protection greater than if the acyl derivatives or the other agents were given alone.

Mercaptoethylamine (cysteamine) may be prepared according to Gabriel, L., *Ber.* 31:2837 (1898); Knorr, R., *Ber.* 36:1281 (1903); Mills et al., *J. Am. Chem. Soc.* 62:1173 (1940), and Wenker et al., *J. Am. Chem. Soc.* 62:1173 (1940). AET may be prepared according to Clinton et al., *J. Am. Chem. Soc.* 70:950 (1948); Funahashi, M., *J. Agric. Chem. Soc. Japan* 27:775 (1953); *Chemical Abstr.* 49:157376 (1955) and Doherty et al., *J. Am. Chem. Soc.* 79:5667 (1957). 5-Hydroxytryptamine can be prepared according to Specter et al., *J. Am. Chem. Soc.* 73:5514 (1951); Hamlin, U.S. Pat. No. 2,715,129 (1955); U.S. Pat. No. 2,947,757 (1960). For a review, see Erspamer in E. Jucker, *Progress in Drug Research* 3:151–367 (1961). WR-2721 and WR-1065 may be obtained from the Walter Reed Army Medical Center, Washington, D.C. For a synthesis of 2-mercaptoethanol, see Woodward, *J. Chem. Soc.* 1892 (1948); Peppel et al., U.S. Pat. No. 2,401,665 (1964); U.S. Pat. No. 3,394,192 (1968). Dithiothreitol may be prepared according to Evans et al., *J. Chem. Soc.* 253 (1949). Glutathione can be prepared according to du Vigneaud et al., *Biochem. Prepar.* 2:87 (1952); Goldschmidt et al., *Ber.* 97:2434 (1964); and Ozawa et al., *Bull. Chem. Soc. Japan* 53:2592 (1980). 2-Mercaptoethanesulfonic acid sodium salt may be prepared according to Schramm et al., *J. Am. Chem. Soc.* 77:6231 (1955); Reppe et al., *Ann.* 601:111 (1956); U.S. Pat. No. 3,567,835 (1971). Nicotinamide may be prepared according to Truchan et al., U.S. Pat. No. 2,993,051 (1961); Gasson et al., U.S. Pat. No. 2,904,552 (1959). Glucans may be isolated from *Saccharomyces* cerevisiae according to Woods et al., *Sci* 142:178 (1978). OK-432 may be isolated from Saito et al., *Infec. Immun* 26:779 (1979). PSK may be isolated from *Coriolus versicolor* according to Otsuka, S., et al., Japanese Patent No. 7,308,489 (1973). *Chemical Abstr.* 80:410259g (1974). Lentinan may be prepared according to Abe et al., *Gann* 74:273 (1983). Schizophyllan may be prepared according to Saito et al., *Infec. Immun* 26:779 (1979). Rhodexman may be prepared according to Elinov, *Int. J. Immun.* 4:265 (1982). Mannozym may be prepared according to Nagy et al., *Gen. Pharm.* 12:A31 (1981). Polymannae Rhoderamine may be extracted from *Rhodotorula rubra* according to Komov, *Vopr. Med. Rhim.* 21:351 (1975).

Cytokines IL-2 and TNF may be prepared according to Godard et al., *J. Imuno. Meth* 70:233 (1984), and Brown, *Photo Sci En.* 22:22 (1978), respectively. Thymic peptides may be isolated according to Tomazic et al., *Proc. Am. Ass. Cancer Res.* 24:196 (1983). Glutathione peroxidase may be isolated according to Aisaka et al., *Agro Biol. Chem.* 47:1107 (1983). Superoxide dismutase can be prepared according to *Bio/Technology* 5:363–365 (1987). Catalase may be isolated according to Lolli, U.S. Pat. No. 2,703,779; Schroeder et al., *Biochim. Biohpys. Acta.* 58:611 (1962); Dan, U.S. Pat. No. 2,992,167 (1961); Faucett et al., U.S. Pat. No. 3,102,081 (1963). Glutathione reductase may be isolated according to Muramatsu et al., *Jap. Soc. Sci. Fisheries* 46:757 (1980). Glutathione transferase may be isolated according to Burgess et al., *Fed. Proc.* 41:1738 (1982). Bis-(3,5-diisopropylsalicylato) copper may be prepared according to Sorenson, *J. Med. Chem.* 27:1747 (1984). 3-Mercapto-2-hydroxypropyl ether of dextran may be prepared according to Wieczorek, *Arch. Immunol. Ther. Exp. (Warsz)* 31:715 (1983). The immunostimulant IL-1 may be prepared according to Krueger et al., *Fed. Proc.* 42:356 (1983). Vitamin A may be extracted from fish liver oil according to Karrer et al., *Helv. Chim. Acta.* 16:625 (1933); Heilvon et al., *Biochem. J.* 26:1178, 1194 (1932). Beta carotene may be isolated from carrots according to Willstatter et al., *Z. Physiol. Chem.* 64:47 (1910); Kuhn et al., *Ber.* 64:1349 (1931); Barnett et al., U.S. Pat. No. 2,848,508 (1958). For preparations of prostaglandins $E_1$, $E_2$, $F_2$, $I_2$ and X see *The Merck Index*, Tenth Edition, Windholz, J., et al. (eds.), Merck and Col., Inc., Rahway, N.J., pp. 7777–7781 (1983). For a preparation of methylene blue see Fierz-David, H. E., et al., *Fundamental Processes of Dye Chemistry*, Interscience, New York, p. 311 (1949). N-arylacetyldehydroalanines may be prepared according to Viehe, H. G., et al., Patent No. WO/02523.

The pharmacologically active acyl derivatives may be combined with suitable pharmaceutically acceptable carriers comprising excipients and auxiliaries which facilitate processing of the active compounds. These can be administered as tablets, dragees, capsules, and suppositories. The compositions can be administered orally, rectally, vaginally, or released through the buccal pouch of the mouth, and may be applied in solution form by injection, orally or by topical administration. The compositions may contain about from 0.1 to 99%, preferably from about 50 to 90% of the active compounds, together with the excipient(s).

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellulose, hydroxypropylmethyl cellulose, sodium carboxymethyl cellulose, and/or polyvinyl pyrrolidone.

If desired, disintegrating agents may be added such as the above-mentioned starches and also carboxymethylstarch, cross-linked polyvinyl pyrrolidone, agar, or algenic acid or a salt thereof, such as sodium alginate.

Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dye stuffs or pigments may be added to the tablets or dragee coatings, for example, for identification or in order to characterize different combinations of compound doses.

Other pharmaceutical preparations which can be used orally include push-fit capsules made of gelatin, as well as soft-sealed capsules made of gelatin and a plasticizer such as glycerol or sorbitol. The push-fit capsules contain the active compound(s) in the form of granules which may be mixed with fillers such as lactose, binders such as starches and/or lubricants such as talc or magnesium stearate, and, optionally, stabilizers. In soft capsules, the active compounds are preferably dissolved or suspended in suitable liquids such as fatty oils, liquid paraffin, or polyethylene glycols. In addition, stabilizers may be added.

Possible pharmaceutical preparations which can be used rectally include, for example, suppositories which consist of a combination of active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water soluble form, for example, water soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may include substances which increase the viscosity of the suspension which include, for example, sodium carboxymethylcellulose, sorbitol, and/or dextran. Optionally, the suspension may also contain stabilizers.

The acyl deoxyribonucleosides may be formulated as part of a skin lotion or suntan lotion for topical administration. Suitable formulations for topical administration include appropriate oily suspensions or solutions. Suitable lipophilic solvents or vehicles include fatty oils, for example sesame oil or coconut oil, or synthetic fatty acid esters, for example ethyl oleate or triglycerides. These topical formulations may be used to treat damaged tissue such as skin wounds or burns, or to treat or prevent sunlight induced cellular damage (sunburn).

For purposes of enhancing wound healing, the compositions of the present invention may be formulated as part of bioerodible microcapsules for topical administration. Such microcapsules may comprise, for example, polylactate or lactate-glycolate copolymers. See Weise, D. L. et al., *Drug Carriers in Biology and Medicine*, Gregoriadis, G. et al., Academic Press, NY p. 237–270 (1979).

The following examples are illustrative, but not limiting of the methods and compositions of the present invention. Other suitable modifications and adaptations of a variety of conditions and parameters normally encountered in clinical therapy which are obvious to the those skilled in the art are within the spirit and scope of this invention.

EXAMPLES OF METHODS TO PREPARE COMPOUNDS OF THE INVENTION

Example 1

Preparation of 3',5'-Diacyl-2'-deoxythymidine From Acid Anhydrides

2'-Deoxythymidine is dissolved in anhydrous pyridine at room temperature. 2.1 molar equivalents of the acid anhydride of the desired acyl compound (e.g., acetic anhydride, lactate anhydride, butyric anhydride, etc.) is then added. The reaction mixture is then heated to 80–85°C. for 1 to 4 hours, cooled, poured into ice water, and the esters recovered by extraction with chloroform or a similar solvent. The chloroform is then washed with ice-cold 0.01 N sulfuric acid, 1% aqueous sodium bicarbonate, and finally water. After drying with sodium sulfate, the chloroform is evaporated and the residual oil or crystals are subjected to chromatography (adapted from Nishizawa et al., *Biochem. Pharmacol.* 14:1605 (1965)).

From Acid Chlorides:

To 2'-deoxythymidine dissolved in anhydrous pyridine is added, at 5° C., 2.1 molar equivalents of the acid chloride of the desired acyl compound (e.g., palmitoyl chloride, acetyl chloride, etc.). The mixture is held at room temperature overnight, added to ice water, and worked up as indicated above (adapted from Nishizawa).

Example 2

Preparation of 5'-Acyl-2'-deoxythymidine

To 2'-deoxythymidine dissolved in anhydrous pyridine is added, at room temperature, 1.0 molar equivalent of the acid anhydride of the desired acyl compound. The reaction is then heated to approximately 80–85° C. for several hours, cooled, poured into ice water, and the esters recovered by extraction with chloroform or a similar solvent. The chloroform is then washed in ice-cold 0.01 N sulfuric acid, 1% aqueous sodium bicarbonate, and finally water. After drying with sodium sulfate, the chloroform is evaporated and the residual oil or crystals are subjected to chromatography. The major product, which is isolated by chromatography is the 5' substituted ester (adapted from Nishizawa et al.

Alternatively, selectively 5' acylation of deoxythymidine may be accomplished by suspending 2'-deoxythymidine in a mixture of pyridine and N,N-dimethylformamide cooled to 0° C. in an ice bath. 1.0 molar equivalent of the acid chloride of the desired acyl compound is added dropwise to the mixture, which is stirred at 9° C. for 12–24 hours. Water is then added to stop the reaction, and then the solvents are evaporated in vacuo at 50° C. The residue is dissolved in methanol and purified by chromatography on silica gel (adapted from Baker et al., *J. Med. Chem.* 21:1218 (1978).

Example 3

Preparation of 3'-Acyl-2'-deoxythymidine

To a stirred suspension of 2'-deoxythymidine in dry N,N-dimethylformamide is added 2.4 molar equivalents of imidazole followed by 1.2 molar equivalents of t-butyldimethylchlorosilane. The mixture is stirred with protection from moisture at room temperature for 20 hours, at which time the solvent is removed at 50° C. in vacuo. The residue is dissolved in 15 ml of ethyl acetate, washed, and evaporated to give a syrup from which is obtained, by crystallization from hot chloroform by the addition of hexane to the point of opalescence, 5'-(t-butyldimethylsilyl)-2'-deoxythymidine.

To a stirred suspension of 5'-(t-butylmethylsilyl)-2'-deoxythymidine in dry pyridine cooled to 0° C. is added 1.1 molar equivalents of the appropriate acid anhydride of the desired acyl compound, and the mixture is stirred with protection from moisture for 20 hours at 0–5° C., at which time the reaction is terminated by addition of a few ml of water. The solvent is evaporated and the residue is extracted and evaporated to give a thick, clear syrup, which is then dried in vacuo at 25° C.

The t-butylmethylsilyl group is removed with glacial acetic acid and tetrabutylammonium fluoride in tetrahydrofuran, yielding the desired 3'-acyl-2'-deoxythymidine derivative (adapted from Baker et al.

Example 4

Preparation of $N^3$-Acyl-2'-deoxythymidine

The acylation of the secondary amine in the 3 position of the pyrimidine ring is accomplished by reacting 3',5'-diacyldeoxythymidine with 1.1 molar equivalents of the acid chloride of the desired acyl substituent in an aprotic solvent (such as ether, dioxane, chloroform, ethyl acetate, acetonitrile, pyridine, dimethylformamide, and the like) in the presence of 1–5 molar equivalents of an organic base (especially aromatic amines such as pyridine, trialkylamines, or N,N-dialkylanilines) (adapted from Fuji et al., U.S. Pat. No. 4,425,335). The acyl substituent on the secondary amine can be the same or different from those on the hydroxyl groups of the ribose moiety.

Example 5

Preparation of 3',5'-Diacyl-2'-deoxycytidine

2-Deoxycytidine hydrochloride is dissolved in N,N-dimethylformamide. 2.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al., *J. Med. Chem.* 14:1159 (1971)).

Example 6

Preparation of 5'-Acyl-2'-deoxycytidine

2-Deoxycytidine hydrochloride is dissolved in N,N-dimethylformamide. 1.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 7

Preparation of $N^4$-Acyl-2'-deoxycytidine

The $N^4$-amino group of 2'-deoxycytidine is the best nucleophile among the amino and hydroxyl functionalities of deoxycytidine. Selective $N^4$-acylation can be accomplished by treating 2'-deoxycytidine with appropriate acid anhydrides in pyridine or a mixture of pyridine and N,N-dimethylformamide. Specifically, deoxycytidine is suspended in pyridine, 1.5 molar equivalents of desired acid anhydride is added, and the mixture is refluxed for about 2 hours. The solvent is removed in vacuo, and the resulting white solid is recrystallized.

Alternatively, 2'-deoxycytidine is dissolved in 70:30 pyridine:n,N-dimethylformamide. 1.5 molar equivalents of the acid anhydride of the desired acyl substituent is added, and the mixture is stirred overnight at room temperature, after which it is poured into water and stirred. The solvent is removed in vacuo to leave a white solid, which is recrystallized (adapted from Sasaki et al., *Chem. Pharm. Bul.* 15:894 (1967)).

An alternative procedure is to dissolve 2'-deoxycytidine in a mixture of water and a water-miscible organic solvent (such as dioxane, acetone, acetonitrile, N,N-dimethylformamide, dimethylsulfoxide, tetrahydrofuran, etc.) and to treat that solution with about a twofold excess of an appropriate acid anhydride. For example, 1 gram of 2'-deoxycytidine, dissolved in 5 ml of water, is mixed with 15 to 100 ml dioxane (more dioxane is needed for more lipophilic substituents), and 2 molar equivalents of the acid anhydride of the desired acyl substituent is added. The mixture is stirred for 5 hours at 80° C. (or for 48 hours at room temperature), and then the solvent is removed in vacuo. The residue is washed with hexane or benzene, and recrystallized (adapted from Akiyama et al., *Chem. Pharm. Bull.* 26:981 (1978)).

Example 8

Preparation of 3',5'$N^4$-Triacyl-2'-deoxycytidine

Compounds in which the acyl substituent of the $N^4$ amino group and the hydroxyl groups of the ribose ring of deoxycytidine are the same (e.g., triacetyl deoxycytidine) are prepared by dissolving or suspending 2'-deoxycytidine in dry pyridine, adding at least 3 molar equivalents of the acid chloride or acid anhydride of the desired substituent, and stirring the mixture overnight at room temperature. The solvent is removed in vacuo and the residue is washed and recrystallized.

Example 9

Preparation of 3',5'-Diacyl-2'-deoxyadenosine

2'-Deoxyadenosine hydrochloride is dissolved in N,N-dimethylformamide. 2.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 10

Preparation of 5'-Acyl-2'-deoxyadenosine

2'-Deoxyadenosine hydrochloride is dissolved in N,N-dimethylformamide. 1.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 11

Preparation of $N^6$-Acyl-2'-deoxyadenosine

The $N^6$-amino group of deoxyadenosine is the best nucleophile among the amino and hydroxyl functionalities of deoxyadenosine. Selective $N^6$-acylation can be accomplished by treatnig 2'-deoxyadenosine with appropriate acid anhydrides in pyridine or a mixture of pyridine and N,N-dimethylformamide. Specifically, deoxyadenosine is suspended in pyridine, 1.5 molar equivalents of desired acid anhydride is added, and the mixture is refluxed for about 2 hours. The solvent is removed in vacuo, and the resulting white solid is recrystallized.

Alternatively, 2'-deoxyadenosine is dissolved in 70:30 pyridine:n,N-dimethylformamide. 1.5 molar equivalents of the acid anhydride of the desired acyl substituent is added, and the mixture is stirred overnight at room temperature, after which it is poured into water and stirred. The solvent is removed in vacuo to leave a white solid, which is recrystallized (adapted from Sasaki et al., *Chem. Pharm. Bul.* 15:894 (1967)).

An alternative procedure is to dissolve 2'-deoxyadenosine in a mixture of water and a water-miscible organic solvent (such as dioxane, acetone, acetonitrile, N,N-dimethylformamide, dimethylsulfoxide, tetrahydrofuran, etc.) and to treat that solution with about a twofold excess of an appropriate acid anhydride. For example, 1 gram of 2'-deoxyadenosine, dissolved in 5 ml of water, is mixed with 15 to 100 ml dioxane (more dioxane is needed for more lipophilic substituents), and 2 molar equivalents of the acid anhydride of the desired acyl substituent is added. The mixture is stirred for 5 hours at 80° C. (or for 48 hours at room temperature), and then the solvent is removed in vacuo. The residue is washed with hexane or benzene, and recrystallized (adapted from Akiyama et al.).

Example 12

Preparation of 3',5'$N^6$-Triacyl-2'-deoxyadenosine

Compounds in which the acyl substituent of the $N^6$ amino group and the hydroxyl group of the ribose ring of deoxyadenosine are the same (e.g., tretraacetyl deoxyadenosine) are prepared by dissolving or suspending 2'-deoxyadenosine in dry pyridine, adding at least 4 molar equivalents of the acid chloride or acid anhydride of the desired substituent, and stirring the mixture overnight at room temperature. The solvent is removed in vacuo and their residue is washed and recrystallized.

Example 13

Preparation of 3',5'-Diacyl-2'-deoxyguanosine

2'-Deoxyguanosine hydrochloride is dissolved in N,N-dimethylformamide. 2.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 14

Preparation of 5'-Acyl-2'-deoxyguanosine

2'-Deoxyguanosine hydrochloride is dissolved in N,N-dimethylformamide. 1.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 15

Preparation of $N^2$-Acyl-2'-deoxyguanosine

The $N^2$-amino group of deoxyguanosine is the best nucleophile among the amino and hydroxyl functionalities of deoxyguanosine. Selective $N^2$-acylation can be accomplished by treatnig 2'-deoxyguanosine with appropriate acid anhydrides in pyridine or a mixture of pyridine and N,N-dimethylformamide. Specifically, deoxyguanosine is suspended in pyridine, 1.5 molar equivalents of desired acid anhydride is added, and the mixture is refluxed for about 2 hours. The solvent is removed in vacuo, and the resulting white solid is recrystallized.

Alternatively, 2'-deoxyguanosine is dissolved in 70:30 pyridine:n,N-dimethylformamide. 1.5 molar equivalents of the acid anhydride of the desired acyl substituent is added, and the mixture is stirred overnight at room temperature, after which it is poured into water and stirred. The solvent is removed in vacuo to leave a white solid, which is recrystallized (adapted from Sasaki et al.).

An alternative procedure is to dissolve 2'-deoxyadenosine in a mixture of water and a water-miscible organic solvent (such as dioxane, acetone, acetonitrile, N,N-dimethylformamide, dimethylsulfoxide, tetrahydrofuran, etc.) and to treat that solution with about a twofold excess of an appropriate acid anhydride. For example, 1 gram of 2'-deoxyadenosine, dissolved in 5 ml of water, is mixed with 15 to 100 ml dioxane (more dioxane is needed for more lipophilic substituents), and 2 molar equivalents of the acid anhydride of the desired acyl substituent is added. The mixture is stirred for 5 hours at 80° C. (or for 48 hours at room temperature), and then the solvent is removed in vacuo. The residue is washed with hexane or benzene, and recrystallized (adapted from Akiyama et al.).

Example 16

Preparation of 3',5'$N^2$-Triacyl-2'-deoxyguanosine

Compounds in which the acyl substituent of the $N^2$ amino group and the hydroxyl groups of the ribose ring of deoxyguanosine are the same (e.g., tretraacetyl deoxyguanosine) are prepared by dissolving or suspending 2'-deoxyguanosine in dry pyridine, adding at least 4 molar equivalents of the acid chloride or acid anhydride of the desired substituent, and stirring the mixture overnight at room temperature. The solvent is removed in vacuo and their residue is washed and recrystallized.

Examples of Clinical Administration Radiation Exposure

Three situations wherein acyl derivatives of deoxyribonucleosides may be clinically useful in treating radiation damage are 1) accidental exposure to ionizing radiation, as in a nuclear accident; 2) exposure to X-radiation during radiography; and 3) radiotherapy of cancer.

In the first case, acyl deoxyribonucleoside derivatives should be administered in a formulation suitable for parenteral injection, followed by oral administration several times per day of doses equivalent to 0.5 to 2 grams of each of the four major deoxyribonucleosides. It is essential that the derivatives of all of the nucleosides be coadministered.

In the second case, X-ray exposure during diagnostic radiography, acyl deoxyribonucleside derivatives are given orally before and after exposure.

In the third case, during cancer radiotherapy, the acyl ribonucleoside derivatives are particularly useful in restoring bone marrow function after its undesirable but unavoidable suppression during irradiation. Moreover, in formulations designed to selectively deliver nucleosides to normal but not neoplastic tissues, the acyl nucleoside derivatives will improve the therapeutic index (ratio of efficacy to toxicity) of the radiation treatment.

Wound Healing

In promoting the healing of skin wounds (whether surgical incisions or accidental wounds), it is best to apply acyl deoxyribonucleoside derivatives topically, either in an ointment or in bioerodible microcapsules. A topical antibiotic might be coadministered. The molar equivalent of 2 to 20 mg of a mixture of all four major deoxyribonucleosides should be applied per square cm of wound area, or 1 to 10 mg per cm of linear incision. The onset of the earliest phases of wound healing in particular is accelerated.

Liver Regneration

Acyl derivatives of deoxyribonucleosides are useful in promoting regeneration of damaged or diseased liver, particularly for accelerating regrowth after surgical removal of a portion of the liver. In this case, oral administration of the derivatives is preferable, in doses corresponding to the molar equivalents of 0.2 to 2 grams of each nucleoside. It is important that derivatives of all four major deoxyribonucleosides be coadministered.

What is claimed is:

1. A method of enhancing the delivery of exogenous deoxyribonucleosides to the tissue of an animal, comprising the step of administering to said animal an effective amount of an acyl derivative of 2'-deoxyadenosine, having the formula

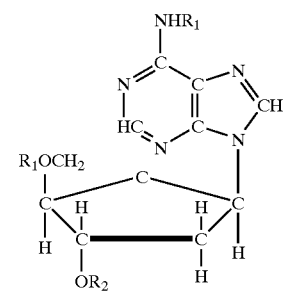

wherein $R_1$, $R_2$, and $R_3$ are the same or different and each is hydrogen or an acyl group derived from
   (a) an unbranched fatty acid with 3 to 22 carbon atoms,
   (b) an amino acid selected from the group consisting of
      glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine, (c) nicotinic acid, or (d) a dicarboxylic acid having 3 to 22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

2. A method of enhancing the delivery of exogenous deoxyribonucleosides to the tissue of an animal, comprising the step of administering to said animal an effective amount of an acyl derivative of 2'-deoxyguanosine having the formula

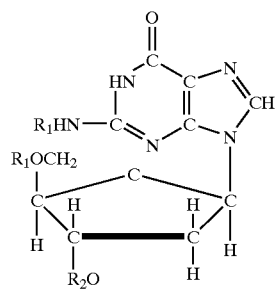

wherein $R_1$, $R_2$, and $R_3$ are the same or different and each is hydrogen or an acyl group derived from (a) an unbranched fatty acid with 3 to 22 carbon atoms, (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, phenylalanine, carnitine, and ornithine, (c) nicotinic acid, or (d) a dicarboxylic acid having 3 to 22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

3. A method of enhancing the delivery of exogenous deoxyribonucleosides to the tissue of an animal, comprising the step of administering to said animal an effective amount of an acyl derivative of 2'-deoxycytidine, having the formula

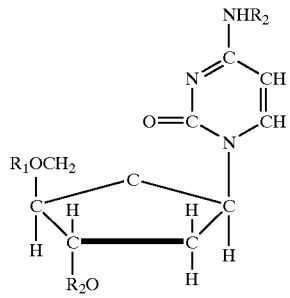

wherein $R_1$, $R_2$, and $R_3$ are the same or different and each is hydrogen or an acyl group derived from (a) an unbranched fatty acid with 3 to 22 carbon atoms, (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine, (c) nicotinic acid, or (d) a dicarboxylic acid having 3 to 22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

4. A method of enhancing the delivery of exogenous deoxyribonucleosides to the tissue of an animal, comprising the step of administering to said animal an effective amount of an acyl derivative of 2'-deoxythymidine, having the formula

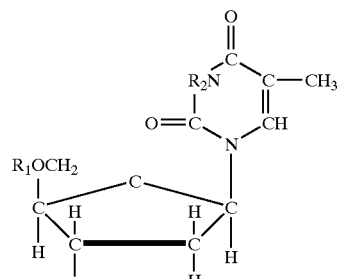

wherein $R_1$ is an acyl group derived from (a) an unbranched fatty acid with 3 to 15 or 17 to 22 carbon atoms, (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine, (c) nicotinic acid, or (d) a dicarboxylic acid having 3 to 22 carbon atoms, and $R_2$ and $R_3$ are H, or a pharmaceutically acceptable salt thereof.

5. A method of enhancing the delivery of exogenus deoxyribonucleosides to the tissue of an animal, comprising the step of administering to said animal an effective amount of an acyl derivative of 2'-deoxythymidine, having the formula

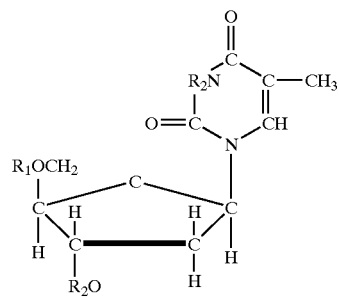

wherein $R_1$ is H, $R_2$ is an acyl group derived from (a) an unbranched fatty acid with 3 to 13 or 15 to 22 carbon atoms, (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine (c) nicotinic acid, or (d) a dicarboxylic acid with 3 to 22 carbon atoms, and $R_3$ is H or a pharmaceutically acceptable salt thereof.

6. A method of enhancing the delivery of exogenous deoxyribonucleosides to the tissue of an animal, comprising the step of administering to said animal an effective amount of an acyl derivative of 2'-deoxythymidine, having the formula

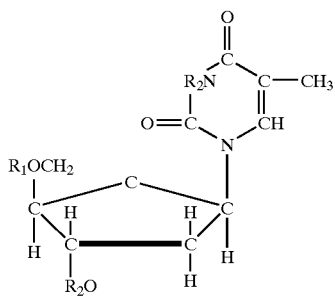

wherein $R_1$ and $R_2$ are the same or different and each is an acyl group derived from
(a) an unbranched fatty acid with 5 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid with 3 to 22 carbon atoms, and $R_3$ is H or a pharmaceutically acceptable salt thereof.

7. A method of enhancing the delivery of exogenous deoxyribonucleosides to the tissue of an animal, comprising the step of administering to said animal an effective amount of an acyl derivative of 2'-deoxythymidine, having the formula

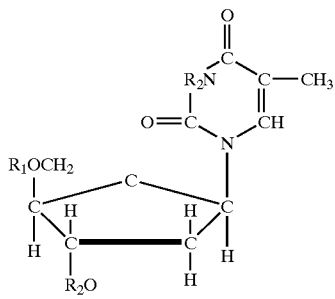

wherein $R_1$, and $R_2$ are the same or different and each is an acyl group derived from
(a) an unbranched fatty acid with 2 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid or
(d) a dicarboxylic acid with 3 to 22 carbon atoms, and $R_3$ is an acyl group derived from an optionally substituted benzoyl or heterocyclic carboxylic acid that is substantially nontoxic, or a pharmaceutically acceptable salt thereof.

8. A method of enhancing the delivery of exogenous deoxyribonucleosides to the tissue of an animal, comprising the step of administering to said animal an effective amount of each of at least two compounds selected from at least two of the groups of compounds having formulae

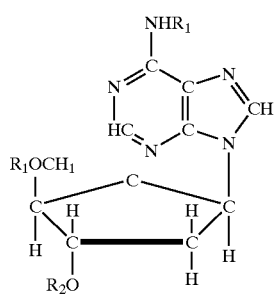
(I)

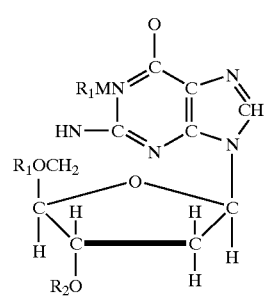
(II)

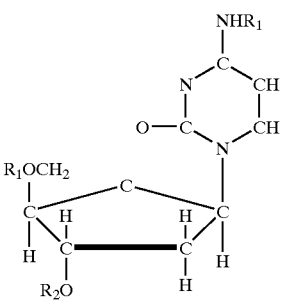
(III)

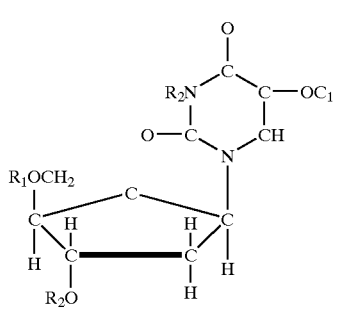
(IV)

wherein $R_1$, $R_2$, and $R_3$ are the same or different and each is H or an acyl group derived from a carboxylic acid, provided that at least one of said substituents $R_1$, $R_2$, and $R_3$ groups of compounds is not hydrogen, or pharmaceutically acceptable salts thereof.

* * * * *